US009656950B2

(12) United States Patent
Hoshino et al.

(10) Patent No.: US 9,656,950 B2
(45) Date of Patent: *May 23, 2017

(54) METHOD FOR PRODUCING OXIME

(71) Applicant: Sumitomo Chemical Company, Limited, Tokyo (JP)

(72) Inventors: Masahiro Hoshino, Oita (JP); Yuta Kikuchi, Osaka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/779,737

(22) PCT Filed: Mar. 17, 2014

(86) PCT No.: PCT/JP2014/057952
§ 371 (c)(1),
(2) Date: Sep. 24, 2015

(87) PCT Pub. No.: WO2014/157020
PCT Pub. Date: Oct. 2, 2014

(65) Prior Publication Data
US 2016/0075639 A1    Mar. 17, 2016

(30) Foreign Application Priority Data

Mar. 27, 2013 (JP) ................. 2013-065655

(51) Int. Cl.
*C07C 249/04* (2006.01)
*C07D 223/10* (2006.01)

(52) U.S. Cl.
CPC .......... *C07C 249/04* (2013.01); *C07D 223/10* (2013.01); *C07C 2101/14* (2013.01); *Y02P 20/582* (2015.11)

(58) Field of Classification Search
CPC .. C07C 251/44; C07C 249/04; C07C 2101/14
See application file for complete search history.

(56) References Cited

U.S. PATENT DOCUMENTS

| | | | |
|---|---|---|---|
| 4,792,620 A * | 12/1988 | Paulik ................. | B01J 31/0231 560/232 |
| 5,026,911 A | 6/1991 | Venturello et al. | |
| 2004/0077903 A1 * | 4/2004 | Suzuki ................. | C07C 249/04 564/267 |
| 2004/0116746 A1 | 6/2004 | Ono et al. | |
| 2006/0229471 A1 | 10/2006 | Suzuki | |
| 2010/0069670 A1 | 3/2010 | Suzuki | |
| 2015/0353478 A1 | 12/2015 | Hoshino et al. | |

FOREIGN PATENT DOCUMENTS

| | | |
|---|---|---|
| CN | 1489574 A | 4/2004 |
| CN | 102627286 A | 8/2012 |
| EP | 1364940 A1 | 11/2003 |
| EP | 2940004 A1 | 11/2015 |
| JP | H02295956 A | 12/1990 |
| JP | H05301858 A | 11/1993 |
| JP | 2003064038 A | 3/2003 |
| JP | 2003212832 A | 7/2003 |
| JP | 2007001952 A | 1/2007 |
| JP | 2008308389 A | 12/2008 |
| JP | 2013189414 A | 9/2013 |
| WO | 02060860 A1 | 8/2002 |
| WO | 2005009613 A1 | 2/2005 |
| WO | 2013125324 A1 | 8/2013 |
| WO | 2014103850 A1 | 7/2014 |

OTHER PUBLICATIONS

Zaragoza Dorwald, Side Reactions in Organic Synthesis, 2005, WILEY-VCH Verlag GmbH & Co. KGaA, Weinheim, Preface. p. IX.*
Varma, Green Chemistry, Solvent-free organic syntheses using supported reagents and microwave irradiation, pp. 43-55.*
International Search Report issued Jun. 3, 2014 in International Application No. PCT/JP2014/057952.
International Preliminary Report on Patentability issued Sep. 29, 2015 in International Application No. PCT/JP2014/057952.
Suzuki et al., "Oxidation of Primary Amines to Oximes with Molecular Oxygen using 1,1-Diphenyl-2-picrylhydrazyl and WO3/Al2O3 as Catalysts", Journal of Organic Chemistry, vol. 78, No. 6, pp. 2301-2310 (2013).
Armor, "The Selective Oxidation of Cyclohexylamine to Its Oxime", Journal of Catalysis, vol. 83, No. 2, pp. 487-490 (1983).
Anilkumar et al., "Gas Phase Beckmann Rearrangement of Cyclohexanone Oxime to e-caprolactam Over Mesoporous and Amorphous NB2O5/Silica Catalysts: A Comparative Study" Catalysis Today, vol. 198, No. 1, pp. 289-299 (2012).
Extended European Search Report issued Oct. 13, 2016 in EP Application No. 14774010.4.
Chen et al., "Direct Synthesis of cyclohexanone oxime from cyclohexanone (II): the effect of surface activity of Ti-PILC on ammoximation," Speciality Chemicals, Issue 1, pp. 44-46 (1996).
Office Action issued Nov. 3, 2016 in CN Application No. 201480016587.3.

* cited by examiner

*Primary Examiner* — Paul A Zucker
(74) *Attorney, Agent, or Firm* — Panitch Schwarze Belisario & Nadel LLP

(57) ABSTRACT

Provided is a method for efficiently producing an oxime, which is a method for producing an oxime by oxidizing, an amine, the method comprising a first contact step and a second contact step, wherein the second contact step is performed by bringing an additional amine into contact with oxygen in the presence of at least a part of an oxidation product obtained in the first contact step.

7 Claims, No Drawings

METHOD FOR PRODUCING OXIME

CROSS-REFERENCE TO RELATED APPLICATION

This application is a Section 371 of International Application No. PCT/JP2014/057952, filed Mar. 17, 2014, which was published in the Japanese language on Oct. 2, 2014, under International Publication No. WO 2014/157020 A1, and the disclosure of which is incorporated herein by reference.

TECHNICAL FIELD

The present invention relates to a method for producing an oxime represented by the formula (II) provided below [hereinafter sometimes referred to as the oxime compound (II)].

BACKGROUND ART

An oxime is useful as a starting material of a lactam, and also a starting material of a synthetic fiber. WO2005/009613 A describes, as a method for producing the oxime compound (II), for example, a method in which a primary amine is oxidized with oxygen using a hydrazyl radical or a hydrazine compound, and a transition metal compound as catalysts.

Problems to be Solved by the Invention

However, the above-mentioned method was not necessarily satisfactory in view of production cost since a large amount of an expensive catalyst is used, so that there has been required to develop a novel method capable of efficiently producing the oxime compound (II). Thus, an object of the present invention is to provide a novel method for efficiently producing the oxime compound (II) without using a large amount of an expensive catalyst.

DISCLOSURE OF THE INVENTION

Means for Solving the Problems

The present inventors have intensively studied so as to achieve the above object, and thus the present invention has been completed.

The present invention includes the following configurations.

(1) A method for producing an oxime represented by the formula (II) provided below, the method comprising the following first contact step and second contact step:

a first contact step: a step of bringing an amine represented by the following formula (I) [hereinafter sometimes referred to as the amine compound (I)]:

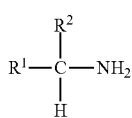

wherein $R^1$ and $R^2$ each independently represent a hydrogen atom, an optionally substituted hydrocarbon group, or an optionally substituted heterocyclic group, provided that $R^1$ and $R^2$ are not simultaneously hydrogen atoms, or $R^1$ and $R^2$, together with the carbon atom to which $R^1$ and $R^2$ are attached, form an optionally substituted alicyclic hydrocarbon group having 3 to 12 carbon atoms, into contact with oxygen in the presence of a first oxidation catalyst to obtain an oxidation product: and a second contact step: a step of bringing an additional amine represented by the above formula (I) into contact with an oxidizing agent in the presence of at least a part of the oxidation product obtained in the first contact step to obtain an oxime represented by the following formula (II):

wherein $R^1$ and $R^2$ are as defined above.

(2) The method according to the above (1), wherein the first contact step is performed in a batch manner or a semibatch manner, and the second contact step is performed in a semibatch manner or a continuous manner.

(3) The method according to the above (1) or (2), wherein the second contact step is performed in the presence of at least one catalyst selected from the group consisting of a second oxidation catalyst and a first oxidation catalyst recovered after the first contact step.

(4) The method according to any one of the above (1) to (3), wherein the first oxidation catalyst is a layered silicate.

(5) The method according to the above (4), wherein the layered silicate is smectite.

(6) The method according to the above (4) or (5), wherein the layered silicate contains at least one selected from the group consisting of hydrogen ions, ammonium ions, quaternary ammonium ions, cations of Group 4 metal elements, cations of Group 5 metal elements, cations of Group 6 metal elements, germanium ions, positively charged oxides of Group 4 metal elements, positively charged oxides of Group 5 metal elements, positively charged oxides of Group 6 metal elements, and positively charged germanium oxides.

(7) The method according to any one of the above (1) to (6), wherein the oxidation product in the first contact step is an oxime represented by the formula (II) and by-product, and the second contact step is a step of further bringing at least a part of by-product obtained in the first contact step, the amine represented by the formula (I), and oxygen into contact with each other to obtain an oxime represented by the formula (II).

(8) A method for producing an amide [hereinafter sometimes referred to as the amine compound (III)] represented by the following formula (III):

wherein $R^1$ and $R^2$ each independently represent a hydrogen atom, an optionally substituted hydrocarbon group, or an optionally substituted heterocyclic group, provided that $R^1$ and $R^2$ are not simultaneously hydrogen atoms, or $R^1$ and $R^2$, together with the nitrogen atom to which $R^1$ is attached and the carbon atom to which $R^2$ is attached, form an optionally substituted aliphatic heterocyclic group having 3 to 12 carbon atoms, the method comprising subjecting an oxime represented by the formula (II) produced by the method according to any one of the above (1) to (7) to a Beckmann rearrangement reaction.

Effects of the Invention

According to the present invention, it is possible to efficiently produce the oxime compound (II).

MODE FOR CARRYING OUT THE INVENTION

The present invention will be described in detail below. The production method of the present invention comprises the first contact step and second contact step described below. In the present invention, the amine compound (I) is brought into contact with an oxidizing agent in the presence of a first oxidation catalyst to obtain an oxidation product as the first contact step.

In the formulas (I), (II), and (III), when $R^1$ and $R^2$ each independently represent a hydrogen atom, an optionally substituted hydrocarbon group, or an optionally substituted heterocyclic group, $R^1$ and $R^2$ are not simultaneously hydrogen atoms. Here, "optionally substituted hydrocarbon group or heterocyclic group" refers to a hydrocarbon group or a heterocyclic group in which hydrogen atoms in a hydrocarbon group or a heterocyclic group may be partially or entirely substituted with another substituent. In $R^1$ and $R^2$, examples of the hydrocarbon group include an alkyl group, an alkenyl group, an alkynyl group, a cycloalkyl group, a cycloalkenyl group, and an aryl group.

The alkyl group is preferably an alkyl group having 1 to 24 carbon atoms, and examples thereof include a methyl group, an ethyl group, a propyl group, an isopropyl group, a butyl group, an isobutyl group, an s-butyl group, a t-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, an eicosyl group, a henicosyl group, a heneicosyl group, a docosyl group, a tricosyl group, and a tetracosyl group.

The alkenyl group is preferably an alkenyl group having 2 to 24 carbon atoms, and examples thereof include a vinyl group, an allyl group, a 2-methylallyl group, an isopropenyl group, a 1-propenyl group, a 1-butenyl group, a 2-butenyl group, a 3-butenyl group, a 1-methyl-1-propenyl group, a 1-methyl-2-propenyl group, a 2-methyl-1-propenyl group, a 2-methyl-2-propenyl group, a 1-pentenyl group, a 2-pentenyl group, a 3-pentenyl group, a 4-pentenyl group, a 1-methyl-1-butenyl group, a 2-methyl-1-butenyl group, a 3-methyl-1-butenyl group, a 1-methyl-2-butenyl group, a 2-methyl-2-butenyl group, a 3-methyl-2-butenyl group, a 1-hexenyl group, a 2-hexenyl group, a 3-hexenyl group, a 4-hexenyl group, a 5-hexenyl group, a 1-methyl-1-pentenyl group, a 2-methyl-1-pentenyl group, a 4-methyl-3-pentenyl group, a 2-ethyl-1-butenyl group, a 2-heptenyl group, a 2-octenyl group, a 2-nonenyl group, a 2-decenyl group, a 2-undecenyl group, a 2-dodecenyl group, a 2-tridecenyl group, a 2-tetradecenyl group, a 2-pentadecenyl group, a 2-hexadecenyl group, a 2-heptadecenyl group, a 2-octadecenyl group, a 2-nonadecenyl group, a 2-icosenyl group, a 2-eicosenyl group, a 2-henicosenyl group, a 2-heneicosenyl group, a 2-dococenyl group, a 2-tricosenyl group, and a 2-tetracosenyl group.

The alkynyl group is preferably an alkynyl group having 2 to 24 carbon atoms, and examples thereof include an ethynyl group, a 1-propynyl group, a 2-propynyl group, a 1-butynyl group, a 2-butynyl group, a 3-butynyl group, a 1-methyl-2-propynyl group, a 1-pentynyl group, a 2-pentynyl group, a 3-pentynyl group, a 4-pentynyl group, a 1-methyl-3-butynyl group, a 2-methyl-3-butynyl group, a 1-hexynyl group, a 2-hexynyl group, a 3-hexynyl group, a 4-hexynyl group, a 5-hexynyl group, a 2-heptynyl group, a 2-octynyl group, a 2-nonynyl group, a 2-decynyl group, a 2-undecynyl group, a 2-dodecynyl group, a 2-tridecynyl group, a 2-tetradecynyl group, a 2-pentadecynyl group, a 2-hexadecynyl group, a 2-heptadecynyl group, a 2-octadecynyl group, a 2-nonadecynyl group, a 2-icosynyl group, a 2-eicosynyl group, a 2-henicosynyl group, a 2-heneicosynyl group, a 2-docosynyl group, a 2-tricosynyl group, and a 2-etracosynyl group.

The cycloalkyl group is preferably a cycloalkyl group having 3 to 8 carbon atoms, and examples thereof include a cyclopropyl group, a cyclobutyl group, a cyclopentyl group, a cyclohexyl group, a cycloheptyl group, and a cyclooctyl group.

The cycloalkenyl group is preferably a cycloalkenyl group having 3 to 8 carbon atoms, and examples thereof include a cyclopropenyl group, a cyclobutenyl group, a cyclopentenyl group, a cyclohexenyl group, a cycloheptenyl group, and a cyclooctenyl group.

Examples of the aryl group include a phenyl group, a naphthyl group, an anthracenyl group, a phenanthryl group, a tolyl group, and a xylyl group.

In $R^1$ and $R^2$, the hydrocarbon group may be optionally substituted. When the hydrocarbon group is an alkyl group, an alkenyl group, or an alkynyl group, examples of the substituent thereof include halogen atoms such as fluorine, chlorine, and bromine atoms; cycloalkyl groups having 3 to 6 carbon atoms, such as a cyclopropyl group, a 1-methylcyclopropyl group, a cyclobutyl group, a cyclopentyl group, a 1-methylcyclopentyl group, and a cyclohexyl group; alkoxy groups having 1 to 4 carbon atoms, such as a methoxy group, an ethoxy group, a propoxy group, an isopropoxy group, a butoxy group, an s-butoxy group, an isobutoxy group, and a t-butoxy group; thioalkoxy group having 1 to 4 carbon atoms, such as a thiomethoxy group, a thioethoxy group, a thiopropoxy group, and a thiobutoxy group; alkenyloxy groups having 3 to 4 carbon atoms, such as an allyloxy group, a 2-propenyloxy group, a 2-butenyloxy group, and a 2-methyl-3-propenyloxy group; aralkyloxy groups having 7 to 20 carbon atoms; aryl groups having 6 to 18 carbon atoms, such as a phenyl group, a naphthyl group, an anthracenyl group, and a phenanthryl group; aryloxy groups such as a phenyloxy group and a naphthyloxy group; alkanoyl groups having 2 to 7 carbon atoms; aryloyl groups having 7 to 19 carbon atoms; and alkoxycarbonyl groups having 1 to 6 carbon atoms. When the hydrocarbon group is an alkyl group, examples of the alkyl group substituted with an aryl group having 6 to 18 carbon atoms include aralkyl groups such as a benzyl group, a phenethyl group, a 3-phenylpropyl group, a benzhydryl group, a trityl group, a triphenylethyl group, a (1-naphthyl)methyl group, and a (2-naphthyl)methyl group.

In $R^1$ and $R^2$, when the hydrocarbon group is a cycloalkyl group, a cycloalkenyl group, or an aryl group, examples of the substituent include the above-mentioned halogen atoms; cycloalkyl groups having 3 to 6 carbon atoms; alkoxy groups having 1 to 4 carbon atoms; thioalkoxy groups having 1 to 4 carbon atoms; alkenyloxy groups having 3 to 4 carbon atoms; aralkyloxy groups having 7 to 20 carbon atoms; aryl groups having 6 to 18 carbon atoms; aryloxy groups; alkanoyl groups having 2 to 7 carbon atoms; aryloyl groups having 7 to 19 carbon atoms; alkoxycarbonyl groups having 1 to 6 carbon atoms; alkyl groups having 1 to 6 carbon atoms, such as a methyl group, an ethyl group, a propyl group, an isopropyl group, a butyl group, an isobutyl group, an s-butyl group, a t-butyl group, a pentyl group, and a hexyl group; alkenyl groups having 2 to 6 carbon atoms, such as a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group; and aralkyl groups having 7 to 20 carbon atoms, such as a benzyl group, a phenethyl group, and a naphthylmethyl group.

In $R^1$ and $R^2$, examples of the heterocyclic group include a heteroaryl group and a heteroaralkyl group. The heteroaryl group is preferably a heteroaryl group having 3 to 9 carbon atoms, and examples thereof include a pyridyl group, a quinonyl group, a pyrrolyl group, an imidazolyl group, a furyl group, an indolyl group, a thienyl group, and an oxazolyl group. The heteroaralkyl group is preferably a heteroaralkyl group having 5 to 10 carbon atoms, and examples thereof include a pyridylmethyl group, a quinolylmethyl group, an indolylmethyl group, a furylmethyl group, and a pyrrolylmethyl group.

In $R^1$ and $R^2$, the heterocyclic group may be optionally substituted. Examples of the substituent in the heterocyclic group include the above-mentioned halogen atoms; cycloalkyl groups having 3 to 6 carbon atoms; alkoxy groups having 1 to 4 carbon atoms; thioalkoxy groups having 1 to 4 carbon atoms; alkenyloxy groups having 3 to 4 carbon atoms; aralkyloxy groups having 7 to 20 carbon atoms; aryl groups having 6 to 18 carbon atoms; aryloxy groups; alkanoyl groups having 2 to 7 carbon atoms; aryloyl groups having 7 to 19 carbon atoms; alkoxycarbonyl groups having 1 to 6 carbon atoms; alkyl groups having 1 to 6 carbon atoms; alkenyl groups having 2 to 6 carbon atoms; and aralkyl groups having 7 to 20 carbon atoms.

In the formula (I), when $R^1$ and $R^2$ each independently represent a hydrogen atom or an optionally substituted hydrocarbon group, examples of the amine compound (I) include methylamine, ethylamine, n-propylamine, isopropylamine, n-butylamine, isobutylamine, s-butylamine, t-butylamine, pentylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, nonadecylamine, icosylamine, eicosylamine, henicosylamine, heneicosylamine, docosylamine, tricosylamine, tetracosylamine, 1-methylbutylamine, 2-methylbutylamine, cyclopropylmethylamine, cyclohexylmethylamine, benzylamine, 2-methylbenzylamine, 4-methylbenzylamine, 1-phenylethylamine, 2-phenylethylamine, 3-aminomethylpyridine, 1-(4-chlorophenyl)ethylamine, 2-(2-chlorophenyl)ethylamine, 1-(3-methoxyphenyl)ethylamine, 1-(4-methoxyphenyl)ethylamine, 2-(2-methoxyphenyl)ethylamine, 2-(3-methoxyphenyl)ethylamine, 2-(4-methoxyphenyl)ethylamine, 1-[3-(trifluoromethyl)phenyl]ethylamine, 1-(1-naphthyl)ethylamine, 1-(2-naphthyl)ethylamine, 1-phenylpropylamine, and 3-phenylpropylamine.

In the formulas (I) and (II), when $R^1$ and $R^2$ are taken together with the carbon atom to which $R^1$ and $R^2$ are attached to form an optionally substituted alicyclic hydrocarbon group having 3 to 12 carbon atoms, the number of carbon atoms is preferably 6 to 12. Here, the alicyclic hydrocarbon group having 3 to 12 carbon atoms refers to an alicyclic hydrocarbon group of 3- to 12-membered ring, and "optionally substituted" refers to an alicyclic hydrocarbon group in which hydrogen atoms in a methylene group in the alicyclic hydrocarbon group may be partially or entirely substituted with another substituent. When substituted with another substituent, the number of carbon atoms of the substituent is not included in the above-mentioned number of carbon atoms. Examples of the substituent in the alicyclic hydrocarbon group having 3 to 12 carbon atoms include the above-mentioned halogen atoms, cycloalkyl groups having 3 to 6 carbon atoms, alkoxy groups having 1 to 4 carbon atoms, thioalkoxy groups having 1 to 4 carbon atoms, alkenyloxy groups having 3 to 4 carbon atoms, aralkyloxy groups having 7 to 20 carbon atoms, aryl groups having 6 to 18 carbon atoms, aryloxy groups, alkanoyl groups having 2 to 7 carbon atoms, aryloyl groups having 7 to 19 carbon atoms, alkoxycarbonyl groups having 1 to 6 carbon atoms, the above-mentioned alkyl groups having 1 to 6 carbon atoms, alkenyl groups having 2 to 6 carbon atoms, and aralkyl groups having 7 to 20 carbon atoms.

In the formulas (I) and (II), when $R^1$ and $R^2$ are taken together with the carbon atom to which $R^1$ and $R^2$ are attached to form an optionally substituted alicyclic hydrocarbon group having 3 to 12 carbon atoms, examples of the amine compound (I) include cyclohexylamine, cyclooctylamine, cyclopentylamine, cycloheptylamine, cyclododecylamine, 2-methylcyclohexylamine, and 4-methylcyclohexylamine.

When cyclohexylamine, of amine compounds (I), is used as a starting material, it is advantageous to employ the method of the present invention in that cyclohexanone oxime is finally obtained in high yield. Cyclohexylamine may be obtained, for example, by hydrogenating aniline, nitrobenzene, nitrocyclohexane, or the like, or may be obtained by an amination reaction of cyclohexene or cyclohexanol with ammonia.

Examples of an oxidizing agent to be used in the first contact step include oxygen and peroxides. Of these oxidizing agents, oxygen is preferable. The oxygen-containing gas is preferably used as an oxygen source of oxygen. This oxygen-containing gas may be air, pure oxygen, or a gas prepared by diluting air or pure oxygen with an inert gas such as nitrogen, argon, or helium. It is also possible to use oxygen-rich air prepared by adding pure oxygen to air. When using the oxygen-containing gas, the oxygen concentration is preferably 1 to 30% by volume. Examples of the peroxide include an inorganic peroxide (hydrogen peroxide, etc.) and an organic peroxide (hydroperoxide, etc.).

Examples of the first oxidation catalyst to be used in the first contact step include a layered silicate, a transition metal compound, and a transition metal compound-supported catalyst. Of these catalysts, a layered silicate is preferable.

In the first contact step, a solvent may also be used. Examples of the solvent include an organic solvent, water, and a mixed solvent of an organic solvent and water. Of these solvents, an organic solvent or a mixed solvent of an organic solvent and water are preferably, and an organic solvent is more preferable. Examples of the organic solvent include alcohols such as methanol, ethanol, propanol, isopropanol, n-butanol, t-butanol, n-hexanol, 2-ethylhexanol, and n-dodecanol; aliphatic hydrocarbons such as pentane, hexane, heptane, octane, petroleum ether, and ligroin; alicyclic hydrocarbons such as cyclopentane, cyclohexane, and methylcyclohexane; aromatic hydrocarbons such as benzene, toluene, o-xylene, m-xylene, and p-xylene; halogenated hydrocarbons such as dichloromethane, chloroform, 1,2-dichloroethane, 1,1,1-trichloroethane, 1,1,2-trichloroethylene, 1,1,2,2-tetrachloroethylene, chlorobenzene, and o-dichlorobenzene; nitriles such as acetonitrile and benzonitrile; nitro compounds such as nitrobenzene; and ester compounds such as ethyl acetate, isopropyl acetate, butyl acetate, and ethyl benzoate and, if necessary, two or more organic solvents can also be used. Of these organic solvents, alcohols, aromatic hydrocarbons, and nitriles are preferably. Of these alcohols, methanol, ethanol, and t-butanol are preferable. Of these aromatic hydrocarbons, toluene, o-xylene, m-xylene, and p-xylene are preferably. Of these nitriles, acetonitrile is preferable.

When using the solvent in the first contact step, the amount is usually 0.1 to 300 parts by weight, and preferably 0.5 to 100 parts by weight, based on 1 part by weight of the amine compound (I).

The first contact step may be performed in a batch manner, a semibatch manner, or a continuous manner, or a manner using a batch manner, a semibatch manner, and a continuous manner in combination. The first contact step is preferably performed in a batch manner or a semibatch manner, and more preferably a semibatch manner, of these manners. The batch manner in the first contact step refers to a reaction manner in which a given amount of an amine compound (I) is reacted with a given amount of oxidizing agent in a reactor in the presence of a first oxidation catalyst for a predetermined time without taking out an oxidation product from the reactor during reaction. The semibatch manner in the first contact step refers to a manner in which a reaction is performed while continuously feeding at least one selected from the group consisting of an amine compound (I), an oxidizing agent, and a first oxidation catalyst into a reactor without taking out an oxidation product from the inside of the reactor during reaction so that an amine compound (I) and an oxidizing agent come into contact with each other in the presence of a first oxidation catalyst in the reactor. When the first contact step is performed in a semibatch manner, the total amount of an amine compound (I), an oxidizing agent, and a first oxidation catalyst may individually be continuously fed to a reactor, or the rest may be continuously fed to the reactor after charging a part thereof into the reactor in advance. When the first contact step is performed by a semibatch manner, those, which are not continuously fed, of an amine compound (I), an oxidizing agent, and a first oxidation catalyst, the total amount thereof may be charged into a reactor in advance. When using oxygen as an oxidizing agent, an oxygen-containing gas is continuously fed to a reactor without taking out an oxidation product from the reactor during reaction, and then an amine compound (I) is brought into contact with oxygen in the oxygen-containing gas in the reactor in the presence of a first oxidation catalyst and an exhaust gas is continuously withdrawn, so that the first contact step can be performed in a semibatch manner. In this case, the total amount of the amine compound (I) and the first oxidation catalyst may individually be continuously fed to a reactor, and then the rest may be continuously fed to the reactor after charging a part thereof into the reactor in advance, or the total amount is charged into the reactor in advance. However, the total amount is preferably charged into a reactor in advance. The continuous manner in the first contact step refers to a manner in which the reaction is performed so that an amine compound (I) and an oxidizing agent come into contact with each other in a reactor in the presence of a first oxidation catalyst while continuously feeding the amine compound (I) and the oxidizing agent, and then an oxidation product is continuously taken out from the inside of the reactor. When the first contact step is performed in a continuous manner, the first oxidation catalyst may be charged into a reactor in advance, or may be continuously fed to a reactor, or may be charged into a reactor in advance and also may be continuously fed to a reactor. When using oxygen as an oxidizing agent, an amine compound (I) and an oxygen-containing gas are continuously fed to a reactor and the amine compound (I) is brought into contact with oxygen in the oxygen-containing gas in the presence of a first oxidation catalyst, and then an oxidation product and an exhaust gas are continuously withdrawn from the inside of the reactor, and thus the first contact step can be performed in a continuous manner. In this case, the first oxidation catalyst may be charged into a reactor in advance, or may be continuously fed to the reactor, or may be charged into a reactor in advance and continuously fed to the reactor. When the first contact step is performed in a continuous manner, the first contact step can be performed in various manners such as a manner in which a liquid phase of a reaction mixture is withdrawn while feeding a reaction starting material in a fixed bed type, fluidized bed type, moving bed type, suspension bed type, stirring/mixing type, or loop type reactor. When the first oxidation catalyst is solid in a reaction mixture and the first contact step is performed in a continuous manner, the first contact step is preferably carried out in a manner in which using a stirring/mixing type reactor, a reaction mixture containing a first oxidation catalyst suspended therein is allowed to exist in a reactor while feeding a reaction starting material in the reactor, and then a liquid phase of the reaction mixture is withdrawn from the reactor through a filter.

The contact temperature in the first contact step is preferably 50 to 200° C., and more preferably 70 to 150° C. The pressure is usually 0.1 to 10 MPa, and preferably 0.2 to 7.0 MPa, in terms of an absolute pressure. The first contact step is preferably preformed under increased pressure. In this case, the pressure may be adjusted using an inert gas such as nitrogen or helium. When the first contact step is carried out in a stirring/mixing type reactor under liquid phase condition using an oxygen-containing gas in a batch manner, a semibatch manner, or a continuous manner, an oxygen-containing gas may be fed to the vapor phase portion of a reactor, or an oxygen-containing gas may be fed to a liquid phase, or an oxygen-containing gas may be fed to the vapor phase portion and a liquid phase of a reactor.

In the first contact step, if necessary, a radical initiator, a phenol-based chain transfer agent, and promoters except for them may be allowed to coexist. Examples of the radical initiator include a hydrazyl radical or a hydrazine compound disclosed in WO 2005/009613 A; an azo compound or a peroxide disclosed in JP 2005-15381 A; and nitroxide. If necessary, two or more radical initiators may be used. Examples of the hydrazyl radical include 2,2-diphenyl-1-picrylhydrazyl and 2,2-di(4-tert-octylphenyl)-1-picrylhydrazyl. Examples of the hydrazine compound include 1,1-diphenyl-2-picrylhydrazine. Examples of the peroxide include diacyl peroxide and, among diacyl peroxides, benzoyl peroxide is preferable. Examples of nitroxide include 2,2,6,6-tetramethylpiperidine-1-oxyl and 4-substituted-2,2,6,6-tetramethylpiperidine-1-oxyl. Examples of the phenol-based chain transfer agent include compounds disclosed in JP 2005-15382 A and, if necessary, two or more phenol-based chain transfer agents may be used. Examples of the promoter except these promoters include an inorganic peroxo acid, salts of an inorganic peroxo acid, and N-halogenated succinimide. If necessary, two or more promoters can also be used. Of these promoters, N-halogenated succinimide is preferable. There is no particular limitation on the inorganic peroxo acid, as long as it is an inorganic oxo acid having an —O—O-bond, and examples thereof include peroxomonosulfuric acid, peroxodisulfric acid, peroxomonocarbonic acid, peroxodicarbonic acid, peroxomonophosphoeric acid, peroxodiphosphoric acid, peroxoboric acid, and peroxonitric acid and, if necessary, two or more acids can also be used. Examples of salts of the inorganic peroxo acid include alkali metal salts (sodium salts, potassium salts, lithium salts, etc.), alkali earth metal salts (magnesium salts, calcium salts, barium salts, etc.), ammonium salts, and quaternary ammonium salts (tetrabutyl ammonium salt, etc.) of the inorganic peroxo acid and, if necessary, two or more salts thereof can also be used. When using potassium peroxomonosulfate as salts of the inorganic peroxo acid, it may be used in the form of Oxone (registered trademark of DuPont Co., mixture of potassium peroxomonosulfate, potassium sulfate, and potassium hydrogen sulfate). Examples of the N-halogenated succinimide include N-bromosuccinimide, N-chlorosuccinimide, and N-iodosuccinimide and, if necessary, two or more salts can also be used. The amounts of the radical initiator and the phenol-based chain transfer agent, and promoters except for them are appropriately set taking production cost and productivity into consideration. When the first contact step is performed in a semibatch manner, the total amount of the radical initiator, phenol-based chain transfer agent, and promoters except for them, may be continuously fed to a reactor, or the rest may be continuously fed to a reactor after charging a part thereof into a reactor in advance, or the total amount may be charged into a reactor in advance. Of these manners, the total amount is preferably charged into a reactor in advance. When the first contact step is performed in a continuous manner, it is preferred that the radical initiator, phenol-based chain transfer agent, and promoters except for them are continuously fed to a reactor, or charged into a reactor in advance and also continuously fed to a reactor.

The amine compound (I) is oxidized by an oxidizing agent and an oxidation product is obtained by the first contact step. The oxidation product is an oxidation product of an oxime compound (II) and others, and examples thereof include a case where the oxime compound (II) is contained as a main product and an oxidation product except for the oxime compound (II) is contained as a by-product. Examples of the by-product include a by-product derived from an amine compound (I), a by-product derived from an oxime compound (II), and a by-product derived from a reaction between an amine compound (I) and an oxime compound (II). Specific examples thereof include a ketone, acetamide, a nitro compound, or a compound obtained by further reacting them. Examples of the by-product obtained when the amine compound (I) is cyclohexylamine include cyclohexanone, N-cyclohexylacetamide, nitrocyclohexane, N-(cyclohexylidene)cyclohexylamine, and dicyclohexylamine.

In the present invention, the below-mentioned second contact step is performed in the presence of at least a part of the above-mentioned oxidation product in the first contact step. When at least a part of the oxidation product is used in the second contact step, at least a part of an oxime compound (II) may also be used in the below-mentioned second contact step, together with at least a part of the above-mentioned by-product, or at least a part of by-product separated by separating by-product from oxidation product containing an oxime compound (II) and the above-mentioned by-product may be used in the second contact step described below.

In the present invention, an amine compound (I) is further brought into contact with oxygen in the presence of at least a part of an oxidation product obtained in the first contact step to obtain an oxime compound (II) as the second contact step. That is, a new amine compound (I), which was not passed through the first contact step, is brought into contact with oxygen in the presence of at least a part of oxidation product obtained in the first contact step to obtain an oxime compound (II). In the second contact step, an oxime compound (II) may be obtained by using in combination with an amine compound (I) which was unreacted in the first contact step. In the first contact step, when using oxygen as an oxidizing agent, oxygen is further used in the second contact step. It is preferred to use an oxygen-containing gas as an oxygen source of oxygen to be used in the second contact step. This oxygen-containing gas may be, for example, air, or pure oxygen, or those prepared by diluting air or pure oxygen with an inert gas such as nitrogen, argon, or helium. It is also possible to use an oxygen-rich air prepared by adding pure oxygen to air. When using the oxygen-containing gas, the oxygen concentration is preferably 1 to 30% by volume.

At least a part of the oxidation product obtained in the first contact step, which is used in the second contact step, may be at least a part of a reaction mixture containing the oxidation product obtained in the first contact step, or at least a part of the oxidation product obtained by separating a part of the oxidation product from a reaction mixture containing the oxidation product obtained in the first contact step, or may be at least a part of a reaction mixture containing the oxidation product remained after separating a part thereof the oxidation product from a reaction mixture containing the oxidation product obtained in the first contact step. In the present invention, regarding the first contact step and the second contact step, the first contact step is composed of a first contact step (a) in which an amine represented by the formula (I) is brought into contact with an oxidizing agent in the presence of a first oxidation catalyst to obtain a reaction mixture containing an oxidation product and a first oxidation catalyst, and a first contact step (b) in which the first oxidation catalyst is recovered from the reaction mixture obtained in the first contact step (a) to obtain a component containing the oxidation product, and at least a part of the oxidation product obtained in first contact step (b) may be used in the second contact step. When the first contact step is composed of the first contact step (a) and the first contact step (b), at least a part of the oxidation product to be subjected to the second contact step may be either at least a part of a component containing the oxidation product, or at least a part of the oxidation product obtained by separating the oxidation product from the component containing the oxidation product.

The second contact step is preferably performed so that the amount of an amine compound (I) existing in the reaction system preferably becomes 1 to 10,000 fold mol, and more preferably 2 to 1,000 fold mol, based on the amount of the oxidation product to be used in terms of the number of mols of the amine compound (I). The amine compound (I) of the oxidation product is converted into the number of mols, for example, by converting the amount of the oxidation product obtained in the first contact step into the number of mols of the amine compound (I) converted in the first contact step in the first contact step. In the second contact step, on the basis of the number of mols of the amine compound (I) converted in the oxidation product obtained in the first contact step, the amount of the oxidation product to be used in the second contact step can be converted into the number of mols of the amine compound (I) from the proportion between the amount of the oxidation product obtained in the first contact step and the amount of the oxidation product to be used in the second contact step. For example, when the first contact step is carried out using 1.0 mol of the amine compound (I) and the amount of the unreacted amine compound (I) recovered after contacting with the oxidizing agent is 0.8 mol, the amount of the oxide obtained by the first contact step becomes 0.2 mol (=1.0 to 0.8) as a result of conversion into the number of mols of the amine compound (I). When 50% by weight of the oxidation product obtained in the first contact step is used in the second contact step, the amount of the oxidation product to be used in the second contact step becomes 0.1 mol (=0.2 mol×50% by weight) as a result of conversion into the number of mols of the amine compound (I).

When the oxidation product obtained in the first contact step is composed of the oxime compound (II) and by-product, the second contact step is preferably performed so that the amount of the amine compound (I) existing in the reaction system becomes 1 to 10,000 fold mol, and more preferably 2 to 1,000 fold mol, based on the amount obtained by converting the amount of by-product to be used into the number of mols of the amine compound (I). Conversion of by-product into the number of mols of the amine compound (I) is performed, for example, by converting the amount of the oxidation product obtained in the first contact step into the number of mols of the amine compound (I) converted into the first contact step, and reducing the number of mols the obtained oxime compound (II) from the number of mols in the first contact step. In the second contact step, on the basis of the number of mols of the amine compound (I) converted in by-product obtained in the first contact step, the amount of by-product to be used in the second contact step can be converted into the number of mols of the amine compound (I) from the proportion between the amount of by-product obtained after the first contact step and the amount of by-product to be used in the second contact step.

Post treatment operations of the reaction mixture containing the oxidation product obtained by the first contact step can be appropriately selected and, if necessary, the oxidation product can be separated by using treatments such as filtration, washing, distillation, crystallization, extraction, recrystallization, and chromatography in combination. The first oxidation catalyst after using in the first contact step may be recovered in a state of a reaction mixture containing the oxidation product obtained in the first contact step and a first oxidation catalyst, or may be recovered by separating a first oxidation catalyst from a reaction mixture containing the oxidation product obtained in the first contact step and a first oxidation catalyst. Apart of a solution containing the oxidation product obtained by separating the first oxidation catalyst from a reaction mixture containing the oxidation product obtained in the first contact step and a first oxidation catalyst may be used as the oxidation product to be used in the second contact step. When the first oxidation catalyst is a solid catalyst in the reaction mixture, the first oxidation catalyst is preferably separated by solid-liquid separation. Examples of the separation method in the solid-liquid separation include known methods such as filtration, sedimentation separation, and centrifugal separation.

The first oxidation catalyst recovered after the first contact step may be recycled to the first contact step or may be used as the catalyst in the second contact step after subjecting to treatments such as washing, calcination, and ion exchange treatment. When the reaction mixture obtained in the first contact step contains a solvent and an unreacted starting material, the recovered solvent and unreacted starting material may be either recycled to the first contact step or used in the second contact step.

In the second contact step, a contact is preferably performed between a further amine compound (I) and oxygen by allowing at least one catalyst selected from the group consisting of a second oxidation catalyst and a first oxidation catalyst recovered after the first contact step to coexist, together with at least a part of the oxidation product obtained in the first contact step. Examples of the second oxidation catalyst include a layered silicate, a transition metal compound, and a transition metal compound-supported catalyst. Of these catalysts, layered silicate is preferable.

The layered silicate, which is preferably used as the first oxidation catalyst or second oxidation catalyst, may be either a natural product or an artificially synthesized synthetic product, or may be a mixture thereof. Examples of the method for synthesizing a synthetic product include a hydrothermal synthesis reaction method, a solid phase reaction method, and a melt synthesis method. Examples of the layered silicate include smectites such as montmorillonite, saponite, beidellite, nontronite, sauconite, stevensite, hectorite, volkonskoite, and swinefordite; vermiculites; micas such as muscovite, phlogopite, annite, eastonite, siderophyllite tetra-ferri-annite, polylithionite, celadonite, ferro-celadonite, ferro-aluminoceladonite, aluminoceladonite, tobelite, and paragonite; brittle micas such as clintonite, bityite, and margarite; chlorites such as clinochlore, chamosite, pennantite, nimite, baileychlore, cookeite, and sudoite; talc; pyrophyllites; kaolinites such as kaolinite, dickite, nacrite, halloysite, amesite, berthierine, cronstedtite, nepouite, kellyite, fraiponite, and brindleyite; and serpentines such as antigorite, chrysotile, and lizardite and, if necessary, two or more layered silicates thereof can also be used. Of these layered silicates, smectite is preferable in view of selectivity of the obtained oxime compound (II).

In the present invention, the layered silicate may be used in the form of a clay mineral containing a layered silicate, and examples of the clay mineral containing a layered silicate include clay minerals containing montmorillonite, such as bentonite, acid clay, and activated clay. The layered silicate may be used after calcination, and the temperature of calcination is preferably 150 to 600° C., and the calcination time is preferably 0.1 to 100 hours. Calcination may be performed in an atmosphere of an oxygen-containing gas such as air, or an atmosphere of an inert gas such as nitrogen, helium, argon, or carbon dioxide. The oxygen-containing gas and inert gas may contain steam. Calcination may be performed in a multi-stage in an atmosphere of an oxygen-containing gas or an inert gas. Calcination may be performed in a fluidized bed type or fixed bed type. The device used in calcination is not particularly limited as long as it is a device capable of heating, and it is possible to use, for example, a hot air circulation calcination furnace, a stationary type calcination furnace, a tunnel furnace, a rotary kiln, a far infrared furnace, a microwave heating furnace, and the like.

The layered silicate preferably contains cations between layers, and examples of the cation include hydrogen ions, ammonium ions, quaternary ammonium ions, cations of alkali metal elements, cations of alkali earth metal elements, cations of Group 3 metal elements, cations of Group 4 metal elements, cations of Group 5 metal elements, cations of Group 6 metal elements, cations of Group 7 metal elements, cations of Group 8 metal elements, cations of Group 9 metal elements, cations of Group 10 metal elements, cations of Group 11 metal elements, cations of Group 12 metal elements, aluminum ions, gallium ions, indium ions, thallium ions, tin ions, lead ions, germanium ions, positively charged oxides of Group 4 metal elements, positively charged oxides of Group 5 metal elements, positively charged oxides of Group 6 metal elements, positively charged oxides of Group 7 metal elements, positively charged oxides of Group 8 metal elements, positively charged oxides of Group 9 metal elements, positively charged oxides of Group 10 metal elements, positively charged oxides of Group 11 metal elements, positively charged oxides of Group 12 metal elements, positively charged oxides of aluminum, positively charged oxides of gallium, positively charged oxides of indium, positively charged oxides of thallium, positively charged oxides of tin, positively charged oxides of lead, and positively charged germanium oxides.

Of these cations in the layered silicate having cations between layers, at least one selected from the group consisting of hydrogen ions, ammonium ions, quaternary ammonium ions, cations of Group 4 metal elements, cations of Group 5 metal elements, cations of Group 6 metal elements, germanium ions, positively charged oxides of Group 4 metal elements, positively charged oxides of Group 5 metal elements, positively charged oxides of Group 6 metal elements, and positively charged germanium oxides are preferable; at least one selected from the group consisting of cations of Group 4 metal elements, germanium ions, positively charged oxides of Group 4 metal elements, and positively charged germanium oxides are more preferable; at least one selected from the group consisting of cations of Group 4 metal elements and positively charged oxides of Group 4 metal elements are still more preferable. Examples of Group 4 metal element include titanium and zirconium. Of these metal elements, titanium is preferable. Examples of the Group 5 metal element include vanadium, niobium, and tantalum. Examples of the Group 6 metal element include chromium, molybdenum, and tungsten.

Smectite used suitably as the layered silicate is a layered compound in which a tetrahedron sheet composed of cation and oxygen, and an octahedron sheet composed of cations and oxygen or hydroxide form a negatively charged monolayer, and cations exist between a monolayer and a monolayer. Generally, it is a layered silicate represented by the following formula (A):

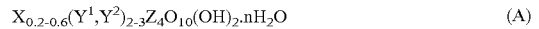

$$X_{0.2-0.6}(Y^1,Y^2)_{2-3}Z_4O_{10}(OH)_2 \cdot nH_2O \quad (A)$$

wherein X represents at least one selected from the group consisting of K⁻, Na⁺, ½Ca²⁺, and ½Mg²⁺, Y¹ represents at least one selected from the group consisting of Mg²⁺, Fe²⁺, Mn²⁺, Ni²⁺, and Zn²⁺, Y² represents at least one selected from the group consisting of Al³⁺, Fe³⁺, Mn³⁺, and Cr³⁺, Z represents at least one selected from the group consisting of Si and Al (excluding the case where Z is Al alone), and n≥0. X represents an interlayer cation, Y¹ and Y² represent cations of an octahedron sheet, and Z represents cations of a tetrahedron sheet.

In the present invention, of smectites, montmorillonite and saponite are preferably used, and montmorillonite is more preferably used.

Montmorillonite used suitably in the present invention is a layered silicate having a 2:1 type structure of silicic acid sheet/aluminic acid sheet/silicic acid sheet as a basic structure of a layer in which the layer is negatively charged by partially substituting aluminum of an aluminic acid sheet with magnesium, and exchangeable cations exist between a layer and a layer, and is generally a layered silicate represented by the following formula (B):

$$X_m(Al_{2-m}Mg_m)Si_4O_{10}(OH)_2 \cdot nH_2O \quad (B)$$

wherein X represents at least one selected from the group consisting of K⁺, Na⁺, ½Ca²⁺, and ½Mg²⁺, 0.2≤m≤0.6, and n≥0. X represents an interlayer cation.

Since the interlayer cation X in smectite or montmorillonite is exchangeable with the other cation, the interlayer cation X is changeable with the other cation by an ion exchange treatment of smectite or montmorillonite. It is preferred to use, as smectite or montmorillonite to be subjected to an ion exchange treatment, those having, as the interlayer cation, at least one selected from the group consisting of sodium ions, potassium ions, and calcium ions. The content of each of sodium ions, potassium ions, and calcium ions in smectite or montmorillonite can be determined by inductively coupled plasma (ICP) emission spectrometry.

It is possible to suitably used, as the layered silicate containing at least one selected from the group consisting of hydrogen ions, ammonium ions, quaternary ammonium ions, cations of Group 4 metal elements, cations of Group 5 metal elements, cations of Group 6 metal elements, germanium ions, positively charged oxides of Group 4 metal elements, positively charged oxides of Group 5 metal elements, positively charged oxides of Group 6 metal elements, and positively charged germanium oxides between layers, which is suitably used in the present invention, those obtained by subjecting a layered silicate having exchangeable cations between layers to an ion exchange treatment.

Examples of the method for preparing a layered silicate containing hydrogen ions as interlayer cations include a method in which a layered silicate having exchangeable cations between layers is subjected to an acid treatment. Examples of an acid used in the acid treatment include inorganic acids such as hydrogen chloride, nitric acid, phosphoric acid, sulfuric acid, and nitrous acid; and organic acids such as acetic acid and trifluoromethanesulfonic acid. Of these acids, the inorganic acid is preferable. Of inorganic acids, hydrogen chloride, nitric acid, and phosphoric acid are preferable. The acid treatment is preferably performed by bringing a layered silicate having exchangeable cations between layers into contact with a solution containing an acid. Interlayer cations are ion-exchanged by the acid treatment, thus enabling the preparation of a layered silicate containing hydrogen ions as the interlayer cation.

The layered silicate containing ammonium ions as the interlayer cation can be prepared, for example, by subjecting a layered silicate having exchangeable cations between layers to ion exchange treatment with at least one selected from the group consisting of ammonia and an ammonium salt. Examples of the ammonium salt include ammonium chloride, ammonium nitrate, ammonium phosphate, ammonium sulfate, and ammonium acetate and, if necessary, two or more ammonium salts thereof can also be used. The ion exchange treatment is preferably performed by bringing a layered silicate having exchangeable cations between layers into contact with at least one selected from the group consisting of ammonia and an ammonium salt. Interlayer cations X are ion-exchanged by ion exchange treatment, thus enabling the preparation of a layered silicate containing ammonium ions as the interlayer cation.

The layered silicate containing quaternary ammonium ion as the interlayer cation can be prepared, for example, by subjecting a layered silicate having exchangeable cations between layers to an ion exchange treatment with a quaternary ammonium compound. Examples of the quaternary ammonium compound include hydroxides and halides of various quaternary ammoniums such as tetramethylammonium, tetraethylammonium, n-propyltrimethylammonium, tetra-n-propylammonium, tetra-n-butylammonium, triethylmethylammonium, tri-n-propylmethylammonium, tri-n-butylmethylammonium, benzyltrimethylammonium, and dibenzyldimethylammonium and, if necessary, two or more quaternary ammonium compounds thereof can also be used. The ion exchange treatment is preferably performed by bringing a layered silicate having cations between layers into contact with a solution containing a quaternary ammonium compound. Interlayer cations are ion-exchanged by the ion exchange treatment, thus enabling the preparation of a layered silicate containing quaternary ammonium ions as the interlayer cation.

Examples of the solvent used in the preparation of the above-mentioned solution containing an acid, solution containing at least one selected from the group consisting of ammonia and an ammonium salt, and solution containing a quaternary ammonium compound include polar solvents such as water, methanol, ethanol, acetone, and 1,2-dimethoxyethane and, if necessary, two or more solvents thereof can also be used. Of these solvents, water is preferable. The amount of the solvent used in appropriately set. When the acid treatment is performed, the solution containing an acid preferably has a pH of 3 or lower.

The acid treatment, the ion exchange treatment with at least one selected from the group consisting of ammonia and an ammonium salt, and the ion exchange treatment with a quaternary ammonium compound may be performed in either a batch or continuous manner. Examples of the method to be performed in a batch manner include a method in which a layered silicate having exchangeable cations between layers is immersed in the above-mentioned solution containing an acid, solution containing at least one selected from the group consisting of ammonia and an ammonium salt, or the solution containing a quaternary ammonium compound in a stirring tank, followed by mixing with stirring. Examples of the method to be performed in a continuous manner include a method in which the above-mentioned solution containing an acid, the solution containing at least one selected from the group consisting of ammonia and an ammonium salt, or solution containing a quaternary ammonium compound is allowed to flow through a tubular container filled with a layered silicate having exchangeable cations between layers; and a method in which a solution phase of a mixture is withdrawn while feeding the above-mentioned solution containing an acid, the solution containing at least one selected from the group consisting of ammonia and an ammonium salt, or the solution containing a quaternary ammonium compound into a stirring tank charged with a layered silicate having exchangeable cations between layers.

The temperature in the above-mentioned acid treatment, or the ion exchange treatment with at least one selected from the group consisting of ammonia and an ammonium salt, or the ion exchange treatment with a quaternary ammonium compound is usually 0 to 150° C., and preferably 20 to 100° C. The time in these treatments is usually 0.1 to 240 hours, and preferably 0.5 to 120 hours. The pressure in these treatments is usually absolute pressure of 0.1 to 1 MPa, and preferably atmospheric pressure. The use amount of the above-mentioned solution containing an acid, the solution containing at least one selected from the group consisting of ammonia and an ammonium salt, or the solution containing a quaternary ammonium compound is appropriately set based on the layered silicate having exchangeable cations between layers. The above-mentioned acid treatment, or the ion exchange treatment with at least one selected from the group consisting of ammonia and an ammonium salt, or the ion exchange treatment with a quaternary ammonium compound may be performed a plurality of times, and these treatment may also be used in combination.

The layered silicate containing, as the interlayer cation, at least one cation selected from the group consisting of cations of Group 4 metal elements, cations of Group 5 metal elements, cations of Group 6 metal elements, and germanium ions can be prepared, for example, by subjecting a layered silicate having exchangeable cations between layers to an ion exchange treatment [hereinafter, the ion exchange treatment is sometimes referred to as an ion exchange treatment with a metal element compound] with at least one compound selected from the group consisting of compounds of Group 4 metal elements, compounds of Group 5 metal elements, compounds of Group 6 metal elements, and germanium compounds. The ion exchange treatment is preferably performed by bringing a layered silicate having exchangeable cations between layers into contact with a solution containing at least one compound selected from the group consisting of compounds of Group 4 metal elements, compounds of Group 5 metal elements, compounds of Group 6 metal elements, and germanium compounds. Interlayer cations are ion-exchanged by the ion exchange treatment, thus enabling the preparation of a layered silicate containing, as the interlayer cation, at least one cation selected from the group consisting of cations of Group 4 metal elements, cations of Group 5 metal elements, cations of Group 6 metal elements, and germanium ions. The content of at least one cation selected from the group consisting of cations of Group 4 metal elements, cations of Group 5 metal elements, cations of Group 6 metal elements, and germanium ions in the layered silicate is preferably 0.01 to 50% by weight, more preferably 0.1 to 25% by weight, and still more preferably 0.2 to 10% by weight. When two or more cations selected from the group consisting of cations of Group 4 metal elements, cations of Group 5 metal elements, cations of Group 6 metal elements, and germanium ions is contained in the layered silicate, the total content thereof may be within the above range. The content of each of cations of Group 4 metal elements, cations of Group 5 metal elements, cations of Group 6 metal elements, and germanium ions can be determined, for example, by inductively coupled plasma (ICP) emission spectrometry.

Examples of the compound of Group 4 metal elements include inorganic compounds of Group 4 metal elements and organic compounds of Group 4 metal elements. Examples of the inorganic compound of Group 4 metal elements include halides of Group 4 metal elements, such as titanium trichloride ($TiCl_3$), titanium tetrachloride ($TiCl_4$), titanium tetrabromide ($TiBr_4$), titanium tetrafluoride ($TiF_4$), titanium tetraiodide ($TiI_4$), zirconium trichloride ($ZrCl_3$), zirconium tetrachloride ($ZrCl_4$), zirconium tribromide ($ZrBr_3$), zirconium tetrabromide ($ZrBr_4$), zirconium tetrafluoride ($ZrF_4$), and zirconiumtetraiodide ($ZrI_4$); nitrates of Group 4 metal elements, such as titanium tetranitrate ($Ti(NO_3)_4$) and zirconium tetranitrate ($Zr(NO_3)_4$); oxynitates of Group 4 metal elements, such as zirconyl nitrate ($ZrO(NO_3)_2$); sulfates of Group 4 metal elements, such as titanium disulfate ($Ti(SO_4)_2$) and zirconium disulfate ($Zr(SO_4)_2$); and phosphates of Group 4 metal elements, such as titanium phosphate ($Ti_3(PO_4)_4$) and zirconium phosphate ($Zr_3(PO_4)_4$). Examples of the organic compound of Group 4 metal elements include alkoxide compounds of Group 4 metal elements, such as $Ti(OR^3)_4$ (hereinafter, $R^3$ represents an alkyl group having 1 to 4 carbon atoms) and $Zr(OR^3)_4$; halogenated alkoxide compounds of Group 4 metal elements, such as $TiCl(OR^3)_3$, $TiCl_2(OR^3)_2$, $TiCl_3(OR^3)$, $ZrCl(OR^3)_3$, $ZrCl_2(OR^3)_2$, and $ZrCl_3(OR^3)$; and acetates of Group 4 metal elements, such as titanium tetraacetate ($Ti(CH_3COO)_4$) and zirconium tetraacetate ($Zr(CH_3COO)_4$). If necessary, hydrates of compounds of Group 4 metal elements may also be used, and two or more hydrates thereof may also be used. Compounds of Group 4 metal elements are preferably halides of Group 4 metal elements, sulfates of Group 4 metal elements, alkoxide compounds of Group 4 metal elements, or oxynitrates of Group 4 metal elements, and more preferably halides of Group 4 metal elements.

Examples of the compound of Group 5 metal elements include inorganic compounds of Group 5 metal elements, and organic compounds of Group 5 metal elements. Examples of the inorganic compound of Group 5 metal elements include halides of Group 5 metal elements, such as vanadium trichloride ($VCl_3$), vanadium tetrachloride ($VCl_4$), vanadium tribromide ($VBr_3$), vanadium trifluoride ($VF_3$), vanadium tetrafluoride ($VF_4$), vanadium triiodide ($VI_3$), niobium trichloride ($NbCl3$), niobium tetrachloride ($NbCl5$), niobium tribromide ($NbBr_3$), niobium pentabromide ($NbBr_5$), niobium pentafluoride ($NbF_5$), niobium pentaiodide ($NbI_5$), tantalum trichloride ($TaCl_3$), tantalum pentachloride ($TaCl_5$), tantalum pentabromide ($TaBr_5$), tantalum pentafluoride ($TaF_5$), and tantalum pentaiodide ($TaI_5$). Examples of the organic compound of Group 5 metal elements include alkoxide compounds of Group 5 metal elements, such as $Nb(OR^3)_5$ and $Ta(OR^3)_5$. If necessary, hydrates of compounds of Group 5 metal elements may also be used, and two or more hydrates thereof may also be used.

Examples of the compound of Group 6 metal elements include inorganic compounds of Group 6 metal elements and organic compounds of Group 6 metal elements. Examples of the inorganic compound of Group 6 metal elements include halides of Group 6 metal elements, such as chromium dichloride ($CrCl_2$), chromium trichloride ($CrCl_3$), chromium dibromide ($CrBr_2$), chromium tribromide ($CrBr_3$), chromium difluoride ($CrF_2$), chromium trifluoride ($CrF_3$), chromium diiodide ($CrI_2$), chromium triiodide ($CrI_3$), molybdenum trichloride ($MoCl_3$), molybdenum pentachloride ($MoCl_5$), molybdenum tribromide ($MoBr_3$), molybdenum tetrafluoride ($MoF_4$), molybdenum hexafluoride ($MoF_6$), tungsten tetrachloride ($WCl_4$), tungsten hexachloride ($WCl_6$), tungsten pentabromide ($WBr_5$), and tungsten hexafluoride ($WF_6$); nitrates of Group 6 metal elements, such as chromium trinitrate ($Cr(NO_3)_3$); and sulfates of Group 6 metal elements, such as chromium(III) sulfate ($Cr_2(SO_4)_3$). Examples of the organic compound of Group 6 metal elements include alkoxide compounds of Group 6 metal elements, such as $Mo(OR^3)_5$, $W(OR^3)_5$, and $W(OR^3)_6$; and acetates of Group 6 metal elements, such as chromium triacetate ($Cr(CH_3COO)_3$). If necessary, hydrates of compounds of Group 6 metal elements may also be used, and two or more hydrates thereof may also be used.

Examples of the germanium compound include inorganic compounds of germanium and organic compounds of germanium. Examples of the inorganic compound of germanium include halides of germanium, such as germanium tetrachloride ($GeCl_4$), germanium tetrabromide ($GeBr_4$), germanium tetrafluoride ($GeF_4$), and germanium tetraiodide ($GeI_4$); and sulfides of germanium, such as germanium sulfide ($GeS$). Examples of the organic compound of germanium include alkoxide compounds of germanium, such as $Ge(OR^3)_4$; and halogenated alkoxide compounds of germanium, such as $GeCl(OR^3)_3$, $GeCl_2(OR^3)_2$, and $GeCl_3(OR^3)$. If necessary, hydrates of germanium may also be used, and two or more hydrates thereof may also be used. Of germanium compounds, halides of germanium and alkoxide compounds of germanium are preferable.

In the above-mentioned ion exchange treatment with a metal element compound, the use amount of at least one compound selected from the group consisting of compounds of Group 4 metal elements, compounds of Group 5 metal elements, compounds of Group 6 metal elements, and germanium compounds is preferably 0.01 to 100 parts by weight, and more preferably 0.05 to 50 parts by weight, based on 100 parts by weight of a layered silicate having exchangeable cations between layers in terms of metal elements contained in at least one compound selected from the group consisting of compounds of Group 4 metal elements, compounds of Group 5 metal elements, compounds of Group 6 metal elements, and germanium compounds. When using two or more compounds selected from the group consisting of compounds of Group 4 metal elements, compounds of Group 5 metal elements, compounds of Group 6 metal elements, and germanium compounds, the total use amount thereof may be within the above range.

When the above-mentioned ion exchange treatment with a metal element compound is performed by bringing a layered silicate having exchangeable cations between layers into contact with a solution containing at least one compound selected from the group consisting of compounds of Group 4 metal elements, compounds of Group 5 metal elements, compounds of Group 6 metal elements, and germanium compounds, examples of the solvent used in the preparation of the solution include polar solvents such as water, methanol, ethanol, acetone, and 1,2-dimethoxyethane and, if necessary, two or more solvents thereof can also be used. It is preferred to use an aqueous acidic solution containing at least one compound selected from the group consisting of compounds of Group 4 metal elements, compounds of Group 5 metal elements, compounds of Group 6 metal elements, and germanium compounds. If an aqueous solution prepared by mixing at least one compound selected from the group consisting of compounds of Group 4 metal elements, compounds of Group 5 metal elements, compounds of Group 6 metal elements, and germanium compounds with water has an acidic pH, the solution thus obtained may be used as it is as the aqueous acidic solution, or may be used after mixing with an acid. If an aqueous solution prepared by mixing at least one compound selected from the group consisting of compounds of Group 4 metal elements, compounds of Group 5 metal elements, compounds of Group 6 metal elements, and germanium compounds with water has not an acidic pH, an aqueous acidic solution obtained by mixing with an acid may be used.

Examples of the acid to be optionally used for the preparation of the aqueous acidic solution include an organic acid and an inorganic acid. Of these acids, an inorganic acid is preferable. Examples of the inorganic acid include hydrogen chloride, sulfuric acid, phosphoric acid, and nitric acid. Of these inorganic acids, hydrogen chloride is preferable. The pH of the aqueous acidic solution is preferably 4 or lower. The aqueous acidic solution may also contain a polar organic solvent such as methanol, ethanol, acetone, or 1,2-dimethoxyethane. When using, as at least one compound selected from the group consisting of compounds of Group 4 metal elements, compounds of Group 5 metal elements, compounds of Group 6 metal elements, and germanium compounds, compounds to be hydrolyzed under acidic condition, such as a hydrolyzable halide, an alkoxide compound, and oxynitrate in the preparation of the aqueous acidic solution, the compound is hydrolyzed to form an oxide, thus enabling the preparation of a layered silicate in which interlayer cations are ion-exchanged with at least one selected from the group consisting of positively charged oxides of Group 4 metal elements, positively charged oxides of Group 5 metal elements, positively charged oxides of Group 6 metal elements, and positively charged germanium oxides. When using, as compounds of Group 4 metal elements, compounds of Group 5 metal elements, and compounds of Group 6 metal elements, two or more compounds of Group 4 metal elements, two or more compounds of Group 5 metal elements, or two or more compounds of Group 6 metal elements, which are hydrolyzed under acidic condition, such as hydrolysable halides, alkoxide compounds, or oxynitrate, where Group 4 metal elements, Group 5 metal elements, or Group 6 metal elements contained in these two or more compounds are not the same among the compounds, it is also possible to form a complex oxide containing, as constituent elements, two or more Group 4 metal elements, two or more Group 5 metal elements, or two or more Group 6 metal elements, thus enabling the introduction of a positively charged complex oxide containing, as interlayer cations, constituent elements such as two or more Group 4 metal elements, two or more Group 5 metal elements, or two or more Group 6 metal elements. When using two or more compounds selected from the group consisting of compounds of Group 4 metal elements, compounds of Group 5 metal elements, compounds of Group 6 metal elements, and germanium compounds, it is possible to introduce a positively charged complex oxide containing, as interlayer cations, constituent elements such as two or more metal elements selected from the group consisting of Group 4 metal elements, Group 5 metal elements, Group 6 metal elements, and germanium.

A solution containing at least one compound selected from the group consisting of compounds of Group 4 metal elements, compounds of Group 5 metal elements, compounds of Group 6 metal elements, and germanium compounds may also contain compounds of the other elements, in addition to compounds of Group 4 metal elements, compounds of Group 5 metal elements, compounds of Group 6 metal elements, and germanium compound. Examples of compounds of other elements include compounds of alkali metal elements, compounds of alkali earth metals, compounds of Group 3 metal elements, compounds of Group 7 metal elements, compounds of Group 8 metal elements, compounds of Group 9 metal elements, compounds of Group 10 metal elements, compounds of Group 11 metal elements, compounds of Group 12 metal elements, aluminum compounds, gallium compounds, indium compounds, thallium compounds, tin compounds, lead compounds, silicon compounds, arsenic compounds, antimony compounds, bismuth compounds, selenium compounds, and tellurium compounds and, if necessary, two or more compounds thereof can also be used.

The above-mentioned ion exchange treatment with a metal element compound may be performed in either a batch or continuous manner. Examples of the method performed in a batch manner method include a method in which a layered silicate having exchangeable cations between layers is immersed in a solution containing at least one compound selected from the group consisting of compounds of Group 4 metal elements, compounds of Group 5 metal elements, compounds of Group 6 metal elements, and germanium compounds in a stirring tank, followed by mixing with stirring. Examples of the method performed in a batch manner method include a method in which a solution containing at least one compound selected from the group consisting of compounds of Group 4 metal elements, compounds of Group 5 metal elements, compounds of Group 6 metal elements, and germanium compounds is allowed to flow through a tubular container filled with a layered silicate having exchangeable cations between layers; and a method in which a liquid phase of a mixture is withdrawn while feeding a solution containing at least one compound selected from the group consisting of compounds of Group 4 metal elements, compounds of Group 5 metal elements, compounds of Group 6 metal elements, and germanium compounds into a stirring tank charged with a layered silicate having exchangeable cations between layers.

The temperature of the above-mentioned ion exchange treatment with a metal element compound is usually 0 to 150° C., preferably 10 to 100° C., and more preferably 30 to 70° C. The time of the ion exchange treatment is usually 0.1 to 240 hours, and preferably 0.5 to 120 hours. The pressure at the time of the ion exchange treatment is usually absolute pressure of 0.1 to 1 MPa, and preferably atmospheric pressure. The use amount of a solution containing at least one compound selected from the group consisting of compounds of Group 4 metal elements, compounds of Group 5 metal elements, compounds of Group 6 metal elements, and germanium compounds is appropriately set based on the layered silicate having exchangeable cations between layers. The above-mentioned ion exchange treatment with a metal element compound may be performed a plurality of times, if necessary. It is also possible to use in combination with at least one treatment selected from the group consisting of the above-mentioned acid treatment, the above-mentioned ion exchange treatment with at least one selected from the group consisting of ammonia and an ammonium salt, and the above-mentioned ion exchange treatment with a quaternary ammonium compound. It is possible to prepare a layered silicate containing at least one selected from the group consisting of hydrogen ions, ammonium ions, quaternary ammonium ions, cations of Group 4 metal elements, cations of Group 5 metal elements, cations of Group 6 metal elements, germanium ions, positively charged oxides of Group 4 metal elements, positively charged oxides of Group 5 metal elements, positively charged oxides of Group 6 metal elements, and positively charged germanium oxides by performing at least one treatment selected from the group consisting of the above-mentioned ion exchange treatment with a metal element compound, the above-mentioned acid treatment, the above-mentioned ion exchange treatment with at least one selected from the group consisting of ammonia and an ammonium salt, and the above-mentioned ion exchange treatment with a quaternary ammonium compound.

It is also possible to subject a layered silicate containing, as the interlayer cation, at least one cation selected from the group consisting of cations of Group 4 metal elements, cations of Group 5 metal elements, cations of Group 6 metal elements, and germanium ion to a contact treatment with the above-mentioned solution containing compounds of the other element. Such contact treatment enables supporting of at least one selected from the group consisting of the other element and compounds of the other element, or the introduction of at least one selected from the group consisting of cations of the other element and positively charged oxides of other element between layers.

The layered silicate obtained, after performing at least one treatment selected from the group consisting of the above-mentioned ion exchange treatment with a metal element compound, the above-mentioned acid treatment, the above-mentioned ion exchange treatment with at least one selected from the group consisting of ammonia and an ammonium salt, and the above-mentioned ion exchange treatment with a quaternary ammonium compound, is subjected to a treatment such as washing or drying, if necessary. If the layered silicate obtained after the treatment is in a slurry state, the layered silicate may be recovered by drying the slurry, or the layered silicate may be recovered by separation with filtration, decantation, or the like, followed by washing and further drying, if necessary. It is preferred that the layered silicate obtained after the treatment is subjected to washing since a layered silicate exhibiting high catalytic activity is obtained. Drying can be performed under either a normal pressure or reduced pressure, and the drying temperature is preferably 20 to 250° C., and the drying time is preferably 0.5 to 100 hours. Drying may be performed in an atmosphere of an oxygen-containing gas such as air, or an atmosphere of an inert gas such as nitrogen, helium, argon, or carbon dioxide.

After drying, calcination may be performed, if necessary. The calcination temperature is preferably 150 to 600° C., and the calcination time is preferably 0.1 to 100 hours. Calcination may be performed in an atmosphere of an oxygen-containing gas such as air, or an atmosphere of an inert gas such as nitrogen, helium, argon, or carbon dioxide. The oxygen-containing gas and inert gas may contain steam. Calcination may be performed in a multi-stage in an atmosphere of an oxygen-containing gas or an inert gas. Calcination may be performed in a fluidized bed type or fixed bed type. The device used in calcination is not particularly limited as long as it is a device capable of heating, and it is possible to use, for example, a hot air circulation calcination furnace, a stationary type calcination furnace, a tunnel furnace, a rotary kiln, a far infrared furnace, a microwave heating furnace, and the like.

The layered silicate may be used after molding, using a binder, or by supporting on a carrier, if necessary. Such molding treatment or supporting treatment may be performed before or after the ion exchange treatment. The molding treatment can be performed, for example, by a method such as extrusion, compression, tableting, fluidization, rolling, or spraying, and it is possible to mold into a desired shape, for example, granule, pellet, sphere, cylinder, plate, ring, clover, or the like.

Regarding a combination of the first oxidation catalyst and the second oxidation catalyst, the same kind of an oxidation catalyst may be used, or different kinds of oxidation catalysts may be used. For example, a layered silicate may be used as the first oxidation catalyst and a transition metal compound may be used as the second oxidation catalyst, and the first oxidation catalyst and the second oxidation catalyst may be simultaneously a layered silicates. In the present invention, it is preferred that a first layered silicate is used as the first oxidation catalyst and a second layered silicate is used as the second oxidation catalyst. When the first oxidation catalyst and the second oxidation catalyst are catalysts of the same kind, the respective compositions may be the same or different.

In the second contact step, a solvent may be used. Examples of the solvent include an organic solvent, water, and a mixed solvent of an organic solvent and water. Of these solvents, an organic solvent or a mixed solvent of an organic solvent and water are preferable, and an organic solvent is more preferable. Examples of the organic solvent include solvents exemplified in the above-mentioned first contact step. Of these organic solvents, an alcohol, an aromatic hydrocarbon, and nitrile are preferable. Of these alcohols, methanol, ethanol and t-butanol are preferable. Among these aromatic hydrocarbons, toluene, o-xylene, m-xylene, and p-xylene are preferably. Of these nitriles, acetonitrile is preferable.

When a solvent is used in the second contact step, the amount of the solvent is usually 0.1 to 300 parts by weight, and preferably 0.5 to 100 parts by weight, based on 1 part by weight of the amine compound (I) existing in the reaction system of the second contact step.

The second contact step may be performed in a batch manner, a semibatch manner, a continuous manner, or a manner using a batch manner, a semibatch manner, and a continuous manner in combination. To perform the second contact step in a semibatch manner or a continuous manner is preferable, and to perform that step in a continuous manner is more preferable in that an oxime compound (II) is obtained with high productivity. The batch manner in the second contact step refers to a reaction manner in which a given amount of an amine compound (I) is reacted with a given amount of oxygen in a reactor for a predetermined time in the presence of at least a part of an oxidation product obtained in the first contact step without taking out an oxime compound (II) from the reactor during reaction. The semibatch manner in the second contact step refers to a manner in which a reaction is performed while continuously feeding at least one selected from the group consisting of an amine compound (I), oxygen, and an oxidation product obtained in the first contact step in a reactor so that an amine compound (I) is contacted with oxygen in the presence of an oxidation product obtained in the first contact step without taking out an oxime compound (II) from the reactor during reaction. When the second contact step is performed in a semibatch manner, the total amount of the amine compound (I), oxygen, and the oxidation product obtained in the first contact step may individually be continuously fed to a reactor, or the rest may be continuously fed to a reactor after charging a part thereof into a reactor in advance. When the first contact step is performed in a semibatch manner, those, which are not continuously fed, of an amine compound (I), oxygen, and an oxidation product obtained in the first contact step, the total amount thereof may be charged into a reactor in advance. When the second contact step is performed using an oxygen-containing gas, the oxygen-containing gas is continuously fed to a reactor without taking out an oxime compound (II) from the reactor during reaction to thereby bring the amine compound (I) into contact with oxygen in the oxygen-containing gas in the presence of an oxidation product obtained in the first contact step, and then an exhaust gas is continuously withdrawn, and thus the second contact step can be performed in a semibatch manner. In this case, the total amount of the amine compound (I) and the oxidation product obtained in the first contact step may individually be continuously fed to a reactor, or the rest may be continuously fed to a reactor after charging a part thereof into a reactor in advance. The total amount may be charged into a reactor in advance and, it is preferred that the total amount is charged into a reactor in advance. The continuous manner in the second contact step refers to a manner in which a reaction is performed while continuously feeding an amine compound (I) and oxygen in a reactor so that the amine compound (I) is contacted with oxygen in the reactor in the presence of an oxidation product obtained in the first contact step, and then an oxime compound (II) is continuously taken out from the inside of the reactor. When the second contact step is performed in a continuous manner, the oxidation product obtained in the first contact step may be charged into a reactor in advance, or may be continuously fed to a reactor, or may be charged into a reactor in advance and also continuously fed to a reactor. When the second contact step is performed using an oxygen-containing gas, the second contact step can be performed in a continuous manner by continuously feeding an amine compound (I) and an oxygen-containing gas to a reactor, bringing the amine compound (I) into contact with an oxygen in the oxygen-containing gas in the reactor, and continuously withdrawing the oxime compound (II) and an exhaust gas from the inside of the reactor in the presence of an oxidation product obtained in the first contact step. In this case, the oxidation product obtained in the first contact step may be charged into a reactor in advance, or may be continuously fed to a reactor, or may be charged into a reactor in advance and also continuously fed to a reactor. When the second contact step is performed in a continuous manner, the second contact step can be carried out by various manners such as withdrawal of a liquid phase of the reaction mixture while feeding a reaction starting material into a fixed bed type, fluidized bed type, moving bed type, suspension type, stirring/mixing type, or loop type reactor.

When the second contact step is performed in a semibatch manner using at least one catalyst selected from the group consisting of a second oxidation catalyst and a first oxidation catalyst recovered after contacting in the first contact step, the total amount of such catalyst may be continuously fed to a reactor, or the rest may be continuously fed to a reactor after charging a part thereof into a reactor in advance, or the total amount may be charged into a reactor in advance. Of these manners, the total amount is preferably charged into a reactor in advance. When the second contact step is performed in a continuous manner using at least one catalyst selected from the group consisting of a second oxidation catalyst and a first oxidation catalyst recovered after contacting in the first contact step, such catalyst may be charged into a reactor in advance, or may continuously fed to a reactor, or may be charged into a reactor in advance and also continuously fed to a reactor. When the second contact step is performed in a continuous manner using at least one catalyst selected from the group consisting of a second oxidation catalyst and a first oxidation catalyst recovered after contacting in the first contact step and such catalyst is in the form of a solid in a reaction mixture, the second contact step is preferably carried out by a manner such as withdrawal of a liquid phase of the reaction mixture from a reactor through a filter while feeding a reaction starting material into the reactor so as to allow the reaction mixture containing the suspended catalyst to exist in the reactor, using a stirring/mixing type reactor. Such catalyst is preferably charged into a reactor in advance without being continuously fed.

The contact temperature in the second contact step is preferably 50 to 200° C., and more preferably 70 to 150° C. The pressure is usually 0.1 to 10 MPa, and preferably 0.2 to 7.0 MPa, in terms of an absolute pressure. The second contact step is preferably performed under increased pressure. In this case, the pressure may be adjusted using an inert gas such as nitrogen or helium. When the second contact step is carried out in a batch manner or continuous manner in a stirring/mixing type reactor under liquid phase condition using an oxygen-containing gas, an oxygen-containing gas may be fed to the vapor phase portion of a reactor, or an oxygen-containing gas may be fed to a liquid phase, or an oxygen-containing gas may be fed to the vapor phase portion or a liquid phase of a reactor.

In the second contact step, a radical initiator, a phenol-based chain transfer agent, and promoters except for them may be allowed to appropriately coexist. Examples of the radical initiator include radical initiators exemplified in the above-mentioned first contact step and, if necessary, two or more radical initiators may be used. Examples of the phenol-based chain transfer agent include phenol-based chain transfer agents exemplified in the above-mentioned first contact step and, if necessary, two or more phenol-based chain transfer agents may be used. Examples of the promoter except for them include promoters exemplified in the above-mentioned first contact step and, if necessary, two or more promoters may be used. Of these, N-halogenated succinimide is preferably used as the promoter except for them. The amounts of the radical initiator and the phenol-based chain transfer agent, and promoters except for them are appropriately set taking production cost and productivity into consideration. When the second contact step is performed in a semibatch manner, the total amount of the radical initiator, phenol-based chain transfer agent, and promoters except for them, may be continuously fed to a reactor, or the rest may be continuously fed to a reactor after charging a part thereof into a reactor in advance, or the total amount may be charged into a reactor in advance. Of these manners, the total amount is preferably charged into a reactor in advance. When the second contact step is performed in a continuous manner, it is preferred that the radical initiator, phenol-based chain transfer agent, and promoters except for them are continuously fed to a reactor, or charged into a reactor in advance and also continuously fed to a reactor.

In the production method of the present invention, it is preferred that the first contact step is performed in a batch manner or a semibatch manner, and the second contact step is performed in a semibatch manner or a continuous manner, it is more preferred that the first contact step is performed in a batch manner or a semibatch manner, and the second contact step is performed in a continuous manner, and it is still more preferred that the first contact step is performed in a semibatch manner, and the second contact step is performed in a continuous manner. When the first contact step is performed in a batch manner or a semibatch manner, the second contact step is performed in a continuous manner, and also a first oxidation catalyst recovered after the first contact step, or a second oxidation catalyst and a first oxidation catalyst recovered after the first contact step are used in the second contact step, the first oxidation catalyst recovered after the first contact step is preferably used in a state of a reaction mixture containing the oxidation product obtained in the first contact step and the first oxidation catalyst. That is, the first contact step is a step in which a reaction mixture containing an oxidation product and a first oxidation catalyst is obtained in a semibatch manner by bringing an amine compound (I) into contact with an oxidizing agent in the presence of a first oxidation catalyst, while the second contact step is preferably a step in which an oxime compound (II) is obtained in a continuous manner by further bringing an amine compound (I) into contact with oxygen in the presence of at least a part of a reaction mixture containing an oxidation product obtained in the first contact step and a first oxidation catalyst. In this case, if necessary, a second oxidation catalyst may be allowed to coexist in the second contact step.

When the first contact step is performed in a semibatch manner, and the second contact step is performed in a continuous manner using the total amount of a reaction mixture containing an oxidation product obtained in the first contact step and a first oxidation catalyst, the first contact step is preferably performed so that the amount of the oxidizing agent to be consumed becomes 0.02 mol or more, and preferably 0.04 mol or more, based on 1 mol of the amine compound (I) used.

Post treatment operations of the reaction mixture containing the oxime compound (II) obtained by the second contact step can be appropriately selected, and the oxime compound (II) can be used for various applications after purifying using treatments such as filtration, washing, distillation, crystallization, extraction, recrystallization, and chromatography in combination. When using at least one catalyst selected from the group consisting of the second oxidation catalyst and the first oxidation catalyst recovered after the first contact step in the second contact step, the catalyst recovered after the second contact step can be recycled to the first contact step and/or the second contact step after subjecting to treatments such as washing, calcination, and ion exchange treatment, if necessary. When the reaction mixture contains a solvent and an unreacted material obtained by the second contact step, the solvent and unreacted material recovered can be reused for the first contact step and/or the second contact step.

The oxime compound (II) thus obtained is suitably used as a starting material for the production of the amide compound (III) after allowing to undergo the Beckmann rearrangement reaction.

When, in the oxime compound (II), $R^1$ and $R^2$ are taken together with the carbon atom to which $R^1$ and $R^2$ are attached to form an optionally substituted alicyclic hydrocarbon group having 3 to 12 carbon atoms, the amide compound (III) obtained by the Beckmann rearrangement reaction of the oxime compound (II), $R^1$ and $R^2$ are taken together with the nitrogen atom to which $R^1$ is attached and the carbon atom to which $R^2$ is attached to form an optionally substituted having 3 to 12 carbon atoms aliphatic heterocycle.

Examples of such Beckmann rearrangement reaction include a method which is performed under liquid phase condition, and a method which is performed under vapor phase condition. Examples of the Beckmann rearrangement reaction under liquid phase condition include, for example, a method which is performed in the presence of strong acid such as fuming sulfuric acid, and can be performed in accordance with the method mentioned in JP 48-4791 A. Examples of the Beckmann rearrangement reaction under vapor phase condition include, for example, a method which is performed in the presence of a solid catalyst such as zeolite, and can be performed in accordance with the method mentioned in JP 5-170732 A. For example, when using cyclohexylamine as the amine compound (I), ε-caprolactam can be produced by the Beckmann rearrangement reaction of cyclohexanone oxime obtained by the oxidation.

EXAMPLES

The present invention will be described by way of the following Examples and Comparative Examples, but it is not construed to limit the present invention thereto. In the following Examples, cyclohexylamine [compound in which $R^1$ and $R^2$ are taken together with the carbon atom to which $R^1$ and $R^2$ are attached to form a cyclohexane ring in the formula (I)] and cyclohexanone oxime [compound in which $R^1$ and $R^2$ are taken together with the carbon atom to which $R^1$ and $R^2$ are attached to form a cyclohexane ring in the formula (II)] in the reaction solution were analyzed by gas chromatography.

Reference Example 1

[Preparation of Catalyst]

In a 1 L eggplant-shaped flask, 531 g of ethanol (manufactured by Wako Pure Chemical Industries, Ltd.) and 35 g of montmorillonite (Kunipia F, manufactured by KUNIMINE INDUSTRIES CO., LTD.) were charged, followed by stirring at room temperature for 5 minutes. While stirring the obtained mixture, 42 g of a 20% by weight titanium trichloride solution (dilute hydrochloric acid solution of $TiCl_3$, manufactured by Wako Pure Chemical Industries, Ltd.) was added dropwise to the mixture. After completion of the dropwise addition, the temperature was raised to 50° C. while stirring the mixture in the eggplant-shaped flask using a water bath, stirring was continued at 50° C. for 6 hours. After 6 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst A (montmorillonite containing titanium ions between layers).

Example 1

[First Contact Step]

In a reactor made of SUS316 (volume: 1 L) equipped with a thermocouple, a stirrer, a gas feed line, a gas discharge line, and a reaction solution withdrawal line, 23.5 g of the catalyst A obtained in Reference Example 1, 106 g (1,069 mmol) of cyclohexylamine (manufactured by Wako Pure Chemical Industries, Ltd.), and 106 g of toluene (manufactured by Wako Pure Chemical Industries, Ltd.) were charged and the vapor phase portion in the reactor was replaced by nitrogen gas. After the reactor was sealed, a nitrogen gas was introduced into the vapor phase portion in the reactor to thereby adjust the pressure in the reactor to 0.90 MPa (gauge pressure). Next, the temperature in the reactor was raised to 120° C. while stirring. The pressure in the reactor was 0.90 MPa (gauge pressure). While continuing to stir, a mixed gas of oxygen and nitrogen (oxygen concentration: 7% by volume) was blown into the liquid phase portion of the mixture in the reactor at a flow rate of 450 mL/minute and allowed to flow in the reactor to thereby start the reaction in a semibatch manner. While keeping the pressure in the reactor at 0.90 MPa (gauge pressure), the reaction was continued for 5 hours with discharging a gas through the gas discharged line from the vapor phase portion in the reactor. Feed of the mixed gas of oxygen and nitrogen was stopped, followed by cooling under a nitrogen gas flow, a reaction mixture A was obtained. Next, a liquid phase of the reaction mixture A was withdrawn through the reaction solution withdrawal line using a filter to obtain 67 g of a filtrate A. The filtrate A was analyzed and then the content of cyclohexylamine and the content of cyclohexanone oxime in the reaction mixture A were calculated based on the results of the analytical values. As a result, the content of cyclohexylamine was 977 mmol and the content of cyclohexanone oxime was 58 mmol. The conversion rate of cyclohexylamine was 9%, the selectivity of cyclohexanone oxime was 63%, and the yield of cyclohexanone oxime was 5%. The amount of the oxidation product (cyclohexanone oxime and by-product) in terms of the number of mols of cyclohexylamine was calculated based on the following equation. As a result, it was 92 mmol. The amount of by-product in terms of the number of mols of cyclohexylamine was calculated. As a result, it was 34 mmol.

Amount [mmol] of oxidation product in terms of number of mols of cyclohexylamine=a−b where a: Charge amount [mmol] of cyclohexylamine b: Content [mmol] of cyclohexylamine in reaction mixture A Amount [mmol] of by-product in terms of number of mols of cyclohexylamine=c−d where c: Amount [mmol] of oxidation product in terms of number of mols of cyclohexylamine d: Content [mmol] of cyclohexanone oxime in reaction mixture A

[Second Contact Step]

To 168.5 g of a mixture (mixed slurry of 23.5 g of the catalyst A and 145 g of a reaction solution used after the above-mentioned [First Contact Step], content of cyclohexylamine: 666 mmol, content of cyclohexanone oxime: 40 mmol, content of oxidation product converted into the number of mols of cyclohexylamine: 63 mmol, the content of by-product converted into the number of mols of cyclohexylamine: 23 mmol) remained in a reactor after recovering 67 g of the filtrate A in the above-mentioned [First Contact Step], 34 g (340 mmol) of clohexylamine (manufactured by Wako Pure Chemical Industries, Ltd.) and 34 g of toluene (manufactured by Wako Pure Chemical Industries, Ltd.) were charged and the vapor phase portion in the reactor was replaced by nitrogen. After the reactor was sealed, a nitrogen gas was introduced into the vapor phase portion in the reactor to thereby adjust the pressure in the reactor to 0.90 MPa (gauge pressure). Next, the temperature in the reactor was raised to 120° C. while stirring. The pressure in the reactor was 0.90 MPa (gauge pressure). While continuing to stir, a mixed gas of oxygen and nitrogen (oxygen concentration: 7% by volume) was blown into the liquid phase portion of the mixture in the reactor at a flow rate of 450 mL/minute and allowed to flow in the reactor to thereby start the reaction in a semibatch manner. While keeping the pressure in the reactor at 0.90 MPa (gauge pressure), the reaction was continued for 5 hours with discharging a gas through the gas discharged line from the vapor phase in the reactor. Feed of the mixed gas of oxygen and nitrogen was stopped, followed by cooling under a nitrogen gas flow, a reaction mixture B was obtained. Next, a liquid phase of the reaction mixture B was withdrawn through the reaction solution withdrawal line using a filter to obtain a filtrate B. The filtrate B was analyzed and then the content of cyclohexylamine and the content of cyclohexanone oxime in the reaction mixture B were calculated based on the results of the analytical values. As a result, the content of cyclohexylamine was 795 mmol and the content of cyclohexanone oxime was 208 mmol. The amount of the oxidation product (cyclohexanone oxime and by-product) in terms of the number of mols of cyclohexylamine obtained by the second contact step was calculated based on the following equation. As a result, it was 211 mmol. The amount of cyclohexanone oxime obtained in second contact step was calculated. As a result, it was 168 mmol. The amount of by-product in terms of the number of mols of cyclohexylamine obtained by the second contact step was calculated based on the following equation. As a result, it was 43 mmol. The conversion rate of cyclohexylamine, the selectivity of cyclohexanone oxime, and the yield of cyclohexanone oxime were calculated from the amount of the oxidation product in terms of the number of mols of cyclohexylamine obtained by second contact step and the amount of cyclohexanone oxime obtained by the second contact step. As a result, the conversion rate of cyclohexylamine was 21%, the selectivity of cyclohexanone oxime was 80%, and the yield of cyclohexanone oxime was 17%.

Amount [mmol] of oxidation product in terms of number of mols of cyclohexylamine obtained by the second contact step=e−f where e: Total charge amount [mmol] of cyclohexylamine in second contact step f: Content [mmol] of cyclohexylamine in reaction mixture B Amount [mmol] of cyclohexanone oxime obtained by second contact step=g−h where g: Content [mmol] of cyclohexanone oxime in reaction mixture B h: Charge amount [mmol] of cyclohexanone oxime in second contact step Amount [mmol] of by-product in terms of number of mols of cyclohexylamine obtained by the second contact step=i−j where i: Amount [mmol] of oxygen product in terms of number of mols of cyclohexylamine obtained by the second contact step j: Amount [mmol] of cyclohexanone oxime obtained by second Example 2

[First Contact Step]

The same operation as in Example 1 [First Contact Step] was performed, except that the use amount of the catalyst A was 15 g in place of 23.5 g, a reaction mixture C was obtained. Next, the reaction mixture C was filtered using a filter to obtain a filtrate C. The filtrate C was analyzed, and the content of cyclohexylamine and the content of cyclohexanone oxime in the reaction mixture C were calculated from the obtained analytic value. As a result, the content of cyclohexylamine was 990 mmol and the content of cyclohexanone oxime was 48 mmol. The conversion rate of cyclohexylamine was 7%, the selectivity of cyclohexanone oxime was 61%, and the yield of cyclohexanone oxime was 4%. In the same manner as in Example 1 [First Contact Step], the amount of the oxidation product (cyclohexanone oxime and by-product) in terms of the number of mols of cyclohexylamine was calculated. As a result, it was 79 mmol. The amount of by-product in terms of the number of mols of cyclohexylamine was calculated. As a result, it was 31 mmol.

[Second Contact Step]

In a reactor made of SUS316 (volume: 1 L) equipped with a thermocouple, a stirrer, a gas feed line, a gas discharge line, and a reaction solution withdrawal line, 15 g of the catalyst A obtained in Reference Example 1, 42 g of the filtrate C (content of cyclohexylamine: 198 mmol, content of cyclohexanone oxime: 10 mmol, content of oxidation product in terms of the number of mols of cyclohexylamine: 16 mmol, content of by-product in terms of the number of mols of cyclohexylamine: 6 mmol) obtained in the above-mentioned [First Contact Step], 85 g (856 mmol) of cyclohexylamine (manufactured by Wako Pure Chemical Industries, Ltd.), and 85 g of toluene (manufactured by Wako Pure Chemical Industries, Ltd.) were charged and the vapor phase portion in the reactor was replaced by nitrogen. After the reactor was sealed, a nitrogen gas was introduced into the vapor phase portion in the reactor to thereby adjust the pressure in the reactor to 0.90 MPa (gauge pressure). Next, the temperature in the reactor was raised to 120° C. while stirring. The pressure in the reactor was 0.90 MPa (gauge pressure). While continuing to stir, a mixed gas of oxygen and nitrogen (oxygen concentration: 7% by volume) was blown into the liquid phase portion of the mixture in the reactor at a flow rate of 450 mL/minute and allowed to flow in the reactor to thereby start the reaction in a semibatch manner. While keeping the pressure in the reactor at 0.90

MPa (gauge pressure), the reaction was continued for 5 hours with discharging a gas through the gas discharged line from the vapor phase portion in the reactor. Feed of the mixed gas of oxygen and nitrogen was stopped, followed by cooling under a nitrogen gas flow, a reaction mixture D was obtained. Next, a liquid phase of the reaction mixture D was withdrawn through the reaction solution withdrawal line using a filter to obtain a filtrate D. The filtrate D was analyzed and then the content of cyclohexylamine and the content of cyclohexanone oxime in the reaction mixture D were calculated based on the results of the analytical value. As a result, the content of cyclohexylamine was 909 mmol and the content of cyclohexanone oxime was 120 mmol. In the same manner as in Example 1 [Second Contact Step], the amount of the oxidation product (cyclohexanone oxime and by-product) in terms of the number of mols of cyclohexylamine obtained in the second contact step was calculated. As a result, it was 145 mmol. The amount of cyclohexanone oxime obtained by the second contact step was calculated. As a result, it was 110 mmol. The amount of by-product in terms of the number of mols of cyclohexylamine obtained in the second contact step was calculated. As a result, it was 35 mmol. The conversion rate of cyclohexylamine, the selectivity of cyclohexanone oxime, and the yield of cyclohexanone oxime were calculated from the amount of the oxidation product in terms of the number of mols of cyclohexylamine obtained by second contact step and the amount of cyclohexanone oxime obtained by the second contact step. As a result, the conversion rate of cyclohexylamine was 14%, the selectivity of cyclohexanone oxime was 76%, and the yield of cyclohexanone oxime was 10%.

Reference Example 2

[Preparation of Catalyst B]

In a 100 mL beaker, 15.9 g of methanol (manufactured by Wako Pure Chemical Industries, Ltd.) and 8.0 g of 2 mol/L hydrochloric acid (manufactured by Wako Pure Chemical Industries, Ltd.) were charged and 33.6 g of tetraethyl orthosilicate (manufactured by Wako Pure Chemical Industries, Ltd.) was added while stirring the obtained mixture. After the temperature was raised to 70° C. while stirring using a water bath, followed by continuous stirring at 70° C. for 1 hour to prepare a solution a. Meanwhile, 48.0 g of 2 mol/L hydrochloric acid (manufactured by Wako Pure Chemical Industries, Ltd.) and 4.8 g of titanium tetraisopropoxide (manufactured by Wako Pure Chemical Industries, Ltd.) were charged into a 100 mL beaker, followed by stirring at room temperature for 1 hour to prepare a solution b.

In a 1 L poly beaker, 250 g of methanol (manufactured by Wako Pure Chemical Industries, Ltd.) and 40.0 g of stevensite (SUMECTON ST, manufactured by KUNIMINE INDUSTRIES CO., LTD.) were charged, followed by stirring at room temperature for 5 minutes. The temperature was raised to 50° C. while stirring the mixture in the poly beaker using a water bath, and then a mixed solution of the total amount of the solution a and the total amount of the solution b was added dropwise over 1 hour. After completion of the dropwise addition, stirring was continued at 50° C. for 6 hours. After 6 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. to prepare a catalyst B.

Example 3

[First Contact Step]

In a reactor made of SUS316 (volume: 350 mL) equipped with a thermocouple, a stirrer, a gas feed line, a gas discharge line, and a reaction solution withdrawal line, 9.0 g of the catalyst B obtained in Reference Example 2, 67 g (0.68 mmol) of cyclohexylamine (manufactured by Wako Pure Chemical Industries, Ltd.), 1.3 g (7.3 mmol) of N-bromosuccinimide (manufactured by Tokyo Chemical Industry Co., Ltd.), 6.7 g (0.37 mol) of water, and 25 g of toluene (manufactured by Wako Pure Chemical Industries, Ltd.) were charged. After the reactor was sealed, a mixed gas of oxygen and nitrogen (oxygen concentration: 4.2% by volume) was introduced into the vapor phase portion in the reactor to thereby adjust the pressure in the reactor to 5 MPa (gauge pressure). While stirring, a mixed gas of oxygen and nitrogen (oxygen concentration: 4.2% by volume) was blown into the liquid phase portion of the mixture in the reactor at a flow rate of 20 L/h and allowed to flow in the reactor. While discharging a gas from the vapor phase portion in the reactor through a gas discharge line, the temperature was raised to 90° C. and then the reaction was performed in a semibatch manner by continuing stirring and flow of the mixed gas at 90° C. for 2 hours. During reaction, the concentration of oxygen in the gas to be discharged through the gas discharge line in the reactor was always measured by an oxygen concentration analyzer (G-102, manufactured by Iijima Electronics Corporation). After performing the reaction for 2 hours, the amount of oxygen consumed relative to cyclohexylamine was calculated from the oxygen feed amount and the oxygen discharge amount. As a result, it was 0.06 (molar ratio) and the results revealed that oxygen was consumed in the amount of 0.06 mol per mol of cyclohexylamine charged into the reactor and the oxidation product was formed. The pressure in the reactor changed within a range of 4.9 to 5.1 MPa (gauge pressure) during reaction.

[Second Contact Step]

After the above-mentioned [First Contact Step], while stirring at 90° C., a mixed gas of oxygen and nitrogen (oxygen concentration: 4.2% by volume) was blown into the liquid phase portion of the mixture in the reactor at a flow rate of 20 L/h. While discharging a gas from the vapor phase portion in the reactor through a gas discharge line, a mixture of cyclohexylamine/N-bromosuccinimide/water/toluene (=67/1.3/6.7/25 in a weight ratio) was continuously fed into the reactor at a flow rate of 25 g/h (retention time: 4 hours). While keeping the pressure in the reactor at 5 MPa (gauge pressure), the liquid phase of the mixture in the reactor was continuously withdrawn at a flow rate of 25 g/h through a sintered metal filter made of stainless steel (SUS316) and the reaction was continued at 90° C. for 24 hours. After 24 hours have elapsed, a liquid phase of the reaction mixture was withdrawn through the reaction solution withdrawal line using a filter to obtain a filtrate. The obtained filtrate was analyzed. As a result, the conversion rate of cyclohexylamine was 19%, the selectivity of cyclohexanone oxime was 81%, and the yield of cyclohexanone oxime was 15%.

Reference Example 3

[Preparation of Catalyst B]

In a 100 mL beaker, 327.50 g of deionized water, 139.91 g of nitric acid, and 15 g of montmorillonite (Kunipia F, manufactured by KUNIMINE INDUSTRIES CO., LTD.) were charged. While stirring the obtained mixture, the temperature was raised to 50° C. and then 18.77 g of a 30% by weight titanium(IV) sulfate solution (Ti(SO$_4$)$_2$, manufactured by Wako Pure Chemical Industries, Ltd.) was added dropwise over 1 hour. After completion of the dropwise addition, stirring was continued at 50° C. for 6 hours. After 6 hours have elapsed, cooling to room temperature was performed and stirring was stopped. A solid was separated by pressure filtration of the obtained mixture, and this solid was washed with water and filtered by pressure filtration and then repeatedly washed until the pH of the washing filtrate becomes 5 or higher. After washing, the obtained solid was dried overnight at 110° C. The obtained dried substance was calcined under air flow at 450° C. for 6 hours to prepare a catalyst C (montmorillonite containing titanium ions between layers).

Example 4

[First Contact Step]

In a reactor made of SUS316 (volume: 350 mL) equipped with a thermocouple, a stirrer, a gas feed line, a gas discharge line, and a reaction solution withdrawal line, 9.0 g of the catalyst C obtained in Reference Example 3, 67 g (0.68 mmol) of cyclohexylamine (manufactured by Wako Pure Chemical Industries, Ltd.), 0.65 g (3.7 mmol) of N-bromosuccinimide (manufactured by Tokyo Chemical Industry Co., Ltd.), 3.35 g (0.19 mol) of water, and 29 g of toluene (manufactured by Wako Pure Chemical Industries, Ltd.) were charged. After the reactor was sealed, a mixed gas of oxygen and nitrogen (oxygen concentration: 4.2% by volume) was introduced into the vapor phase portion in the reactor to thereby adjust the pressure in the reactor to 5 MPa (gauge pressure). While stirring, a mixed gas of oxygen and nitrogen (oxygen concentration: 4.2% by volume) was blown into the liquid phase portion of the mixture in the reactor at a flow rate of 20 L/h and allowed to flow in the reactor. While discharging a gas from the vapor phase portion in the reactor through a gas discharge line, the temperature was raised to 90° C. and then the reaction was performed in a semibatch manner by continuing stirring and flow of the mixed gas at 90° C. for 2 hours. During reaction, the concentration of oxygen in the gas to be discharged through the gas discharge line in the reactor was always measured by an oxygen concentration analyzer (G-102, manufactured by Iijima Electronics Corporation). After performing the reaction for 2 hours, the amount of oxygen consumed relative to cyclohexylamine was calculated from the oxygen feed amount and the oxygen discharge amount. As a result, it was 0.05 (molar ratio) and the results revealed that oxygen was consumed in the amount of 0.05 mol per mol of cyclohexylamine charged into the reactor and the oxidation product was formed. The pressure in the reactor changed within a range of 4.9 to 5.1 MPa (gauge pressure) during reaction.

[Second Contact Step]

After the above-mentioned [First Contact Step], while stirring at 90° C., a mixed gas of oxygen and nitrogen (oxygen concentration: 4.2% by volume) was blown into the liquid phase portion of the mixture in the reactor at a flow rate of 20 L/h. While discharging a gas from the vapor phase portion in the reactor through a gas discharge line, a mixture of cyclohexylamine/N-bromosuccinimide/water/toluene (~67/0.65/3.35/29 in a weight ratio) was continuously fed into the reactor at a flow rate of 25 g/h (retention time: 4 hours). While keeping the pressure in the reactor at 5 MPa (gauge pressure), the liquid phase of the mixture in the reactor was continuously withdrawn at a flow rate of 25 g/h through a sintered metal filter made of stainless steel (SUS316) and the reaction was continued at 90° C. for 24 hours. After 24 hours have elapsed, a liquid phase of the reaction mixture was withdrawn through the reaction solution withdrawal line using a filter to obtain a filtrate. The obtained filtrate was analyzed. As a result, the conversion rate of cyclohexylamine was 18%, the selectivity of cyclohexanone oxime was 85%, and the yield of cyclohexanone oxime was 15%.

INDUSTRIAL APPLICABILITY

According to the above-mentioned production method, it is possible to efficiently produce an oxime compound (II).

The invention claimed is:

1. A method for producing an oxime having formula (II) provided below, the method comprising the following first contact step and second contact step:

a first contact step: in a first reactor, bringing an amine having formula (I):

wherein R$^1$ and R$^2$ are each independently a hydrogen atom, an optionally substituted hydrocarbon group, or an optionally substituted heterocyclic group, provided that R$^1$ and R$^2$ are not simultaneously hydrogen atoms, or R$^1$ and R$^2$, together with the carbon atom to which R$^1$ and R$^2$ are attached, form an optionally substituted alicyclic hydrocarbon group having 3 to 12 carbon atoms, into contact with an oxidizing agent in the presence of a first oxidation catalyst comprising a layered silicate to obtain an oxidation product: and a second contact step: in a second reactor, bringing an additional quantity of the amine having formula (I) into contact with an oxidizing agent in the presence of at least a part of the oxidation product obtained in the first contact step to obtain an oxime having formula (II):

wherein R$^1$ and R$^2$ are as defined above.

2. The method according to claim 1, wherein the first contact step is performed in a batch manner or a semibatch manner, and the second contact step is performed in a semibatch manner or a continuous manner.

3. The method according to claim 1, wherein the second contact step is performed in the presence of at least one catalyst selected from the group consisting of a second oxidation catalyst and a first oxidation catalyst recovered after the first contact step.

4. The method according to claim 1, wherein the layered silicate is smectite.

5. The method according to claim 1, wherein the layered silicate contains at least one selected from the group consisting of hydrogen ions, ammonium ions, quaternary ammonium ions, cations of Group 4 metal elements, cations of Group 5 metal elements, cations of Group 6 metal elements, germanium ions, positively charged oxides of Group 4 metal elements, positively charged oxides of Group 5 metal elements, positively charged oxides of Group 6 metal elements, and positively charged germanium oxides.

6. The method according to any one of claim 1, wherein the oxidation product in the first contact step comprises an oxime having formula (II) and a product, and the second contact step is a step of further bringing at least a part of a by-product obtained in the first contact step, the amine having formula (I), and oxygen into contact with each other to obtain an oxime having formula (II).

7. A method for producing an amide having formula (III):

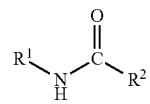

(III)

wherein $R^1$ and $R^2$ are each independently a hydrogen atom, an optionally substituted hydrocarbon group, or an optionally substituted heterocyclic group, provided that $R^1$ and $R^2$ are not simultaneously hydrogen atoms, or $R^1$ and $R^2$, together with the nitrogen atom to which $R^1$ is attached and the carbon atom to which $R^2$ is attached, form an optionally substituted aliphatic heterocyclic group having 3 to 12 carbon atoms, the method comprising subjecting an oxime represented by the formula (II) produced by the method according to claim 1 to a Beckmann rearrangement reaction.

* * * * *